(12) United States Patent
Niedermeyer

(10) Patent No.: US 9,434,006 B2
(45) Date of Patent: *Sep. 6, 2016

(54) COMPOSITION CONTAINING SPHERICAL AND CORAL-SHAPED NANOPARTICLES AND METHOD OF MAKING SAME

(71) Applicant: ATTOSTAT, INC., Salt Lake City, UT (US)

(72) Inventor: William Harold Niedermeyer, West Jordan, UT (US)

(73) Assignee: ATTOSTAT, INC., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/861,318

(22) Filed: Sep. 22, 2015

(65) Prior Publication Data

US 2016/0082513 A1 Mar. 24, 2016

Related U.S. Application Data

(60) Provisional application No. 62/054,221, filed on Sep. 23, 2014.

(51) Int. Cl.
*B82Y 30/00* (2011.01)
*B22F 9/04* (2006.01)
(Continued)

(52) U.S. Cl.
CPC .............. *B22F 9/04* (2013.01); *A01N 59/16* (2013.01); *A61K 9/16* (2013.01); *A61K 9/1682* (2013.01); *A61K 33/38* (2013.01); *B22F 1/0044* (2013.01);
(Continued)

(58) Field of Classification Search
CPC ........................... B82Y 30/00; B22F 2298/10
See application file for complete search history.

(56) References Cited

U.S. PATENT DOCUMENTS

| 4,515,740 A | 5/1985 | Schuettenberg et al. |
| 5,227,608 A | 7/1993 | Yoshida |

(Continued)

FOREIGN PATENT DOCUMENTS

| CN | 102120619 | 7/2011 |
| CN | 103891558 | 7/2014 |

(Continued)

OTHER PUBLICATIONS

Badawy et al., "Surface Charge-Dependent Toxicity of Silver Nanoparticles", Environ. Sci. Technol. 2011, 45, 283-287.
(Continued)

*Primary Examiner* — Carlos Azpuru
(74) *Attorney, Agent, or Firm* — Workman Nydegger

(57) ABSTRACT

Nanoparticle compositions include a plurality of spherical-shaped nanoparticles and a plurality of coral-shaped metal nanoparticles, each coral-shaped metal nanoparticle having a non-uniform cross section and a globular structure formed by multiple, non-linear strands joined together without right angles. The nanoparticle compositions can be one-part or multi-part compositions. Nanoparticle compositions can have a mass ratio of spherical-shaped to coral-shaped nanoparticles of about 5:1-20:1, about 7.5:1-15:1, about 9:1-11:1, or about 10:1 and/or a number ratio of spherical-shaped to coral-shaped nanoparticles of about 50:1-200:1, about 75:1-150:1, about 90:1-110:1 or about 100:1. The nanoparticle compositions can be used for various purposes, including as an antimicrobial (e.g., anti-viral, anti-bacteria, or anti-fungal composition), fuel additive, or treating fabrics.

20 Claims, 11 Drawing Sheets

(51) Int. Cl.

| | | |
|---|---|---|
| *A01N 59/16* | (2006.01) | |
| *A61K 33/38* | (2006.01) | |
| *A61K 9/16* | (2006.01) | |
| *C10L 1/12* | (2006.01) | |
| *B23K 26/36* | (2014.01) | |
| *B23K 26/40* | (2014.01) | |
| *B22F 1/00* | (2006.01) | |
| *B23K 26/03* | (2006.01) | |
| *B23K 26/12* | (2014.01) | |
| *B82Y 5/00* | (2011.01) | |
| *B82Y 99/00* | (2011.01) | |
| *B82Y 40/00* | (2011.01) | |

(52) U.S. Cl.
CPC ........... *B22F 1/0048* (2013.01); *B23K 26/032* (2013.01); *B23K 26/0622* (2015.10); *B23K 26/082* (2015.10); *B23K 26/122* (2013.01); *B23K 26/123* (2013.01); *B23K 26/127* (2013.01); *B23K 26/362* (2013.01); *B23K 26/40* (2013.01); *B82Y 30/00* (2013.01); *C10L 1/1208* (2013.01); *B22F 2202/05* (2013.01); *B22F 2202/06* (2013.01); *B22F 2202/11* (2013.01); *B22F 2301/255* (2013.01); *B22F 2304/054* (2013.01); *B22F 2998/10* (2013.01); *B23K 2203/08* (2013.01); *B23K 2203/14* (2013.01); *B23K 2203/26* (2015.10); *B82Y 5/00* (2013.01); *B82Y 40/00* (2013.01); *B82Y 99/00* (2013.01); *C10L 2200/0209* (2013.01); *Y10S 44/00* (2013.01); *Y10S 514/00* (2013.01)

(56) References Cited

U.S. PATENT DOCUMENTS

| | | | |
|---|---|---|---|
| 5,390,864 | A | 2/1995 | Alexander |
| 5,585,020 | A | 12/1996 | Becker et al. |
| 6,509,070 | B1 | 1/2003 | Voevodin et al. |
| 7,014,737 | B2 | 3/2006 | Harutyunyan et al. |
| 7,371,457 | B2 | 5/2008 | Oldenburg et al. |
| 7,374,730 | B2 | 5/2008 | Simard et al. |
| 7,384,560 | B2 | 6/2008 | Martens et al. |
| 7,509,993 | B1 | 3/2009 | Turng et al. |
| 7,553,801 | B2 | 6/2009 | Alexander et al. |
| 7,662,731 | B2 | 2/2010 | Itoh et al. |
| 7,682,970 | B2 | 3/2010 | Grigoropoulos et al. |
| 7,700,032 | B1 | 4/2010 | Lu et al. |
| 7,884,160 | B2 | 2/2011 | Wang et al. |
| 7,985,367 | B2 | 7/2011 | Hiromatsu et al. |
| 8,685,293 | B1 | 4/2014 | Coppa et al. |
| 2003/0086859 | A1 | 5/2003 | Kawakami et al. |
| 2003/0102099 | A1 | 6/2003 | Yadav et al. |
| 2004/0214001 | A1 | 10/2004 | Oldenburg et al. |
| 2006/0142853 | A1 | 6/2006 | Wang et al. |
| 2007/0287202 | A1 | 12/2007 | Maehashi et al. |
| 2008/0035682 | A1 | 2/2008 | Coffey et al. |
| 2008/0161631 | A1 | 7/2008 | Axtell et al. |
| 2008/0263940 | A1 | 10/2008 | Parish et al. |
| 2009/0246530 | A1 | 10/2009 | Murakami et al. |
| 2010/0050872 | A1 | 3/2010 | Lee |
| 2010/0072645 | A1 | 3/2010 | Hiromatsu et al. |
| 2010/0180413 | A1 | 7/2010 | Jeong |
| 2010/0183739 | A1 | 7/2010 | Newman |
| 2010/0187091 | A1 | 7/2010 | Pierce et al. |
| 2010/0196192 | A1 | 8/2010 | Liu et al. |
| 2011/0052460 | A1 | 3/2011 | Coffey et al. |
| 2011/0193025 | A1 | 8/2011 | Ichikawa et al. |
| 2011/0228890 | A1 | 9/2011 | Dean et al. |
| 2011/0244056 | A1 | 10/2011 | Santra |
| 2012/0088066 | A1 | 4/2012 | Aytug et al. |
| 2012/0136164 | A1 | 5/2012 | Ying et al. |
| 2012/0138862 | A1 | 6/2012 | Hogan |
| 2012/0164073 | A1 | 6/2012 | Xu et al. |
| 2012/0174472 | A1 | 7/2012 | Mills |
| 2012/0301531 | A1 | 11/2012 | Uhlmann et al. |
| 2013/0001833 | A1 | 1/2013 | Niedermeyer |
| 2013/0334104 | A1 | 12/2013 | Halas et al. |
| 2014/0274830 | A1 | 9/2014 | Pol et al. |
| 2014/0288194 | A1 | 9/2014 | Niedermeyer |

FOREIGN PATENT DOCUMENTS

| | | |
|---|---|---|
| CN | 104014811 | 9/2014 |
| WO | WO2013141879 | 9/2013 |

OTHER PUBLICATIONS

U.S. Appl. No. 14/861,243, filed Sep. 22, 2015, Office Action dated Mar. 9, 2016.
U.S. Appl. No. 13/175,708, filed Jul. 1, 2011, Final Office Action dated Mar. 28, 2016.
U.S. Appl. No. 14/298,593, filed Jun. 6, 2014, Neidermeyer.
U.S. Appl. No. 14/861,243, filed Sep. 22, 2015, Neidermeyer.
U.S. Appl. No. 14/861,375, filed Sep. 22, 2015, Neidermeyer.
U.S. Appl. No. 14/861,442, filed Sep. 22, 2015, Neidermeyer.
U.S. Appl. No. 14/861,500, filed Sep. 22, 2015, Neidermeyer.
U.S. Appl. No. 14/861,562, filed Sep. 22, 2015, Neidermeyer.
Chien et al., "Synthesis of nanoparticles: sunlight formation of gold nanodecahedra for ultra-sensitive lead-ion detection", Green Chem., vol. 13, pp. 1162-1166, May 2011.
International Search Report for PCT App. No. PCT/US2015/051642 dated Dec. 14, 2015.
International Search Report for PCT App. No. PCT/US2015/051638 dated Dec. 17, 2015.
International Search Report for PCT App. No. PCT/US2015/051640 dated Dec. 17, 2015.
International Search Report for PCT App. No. PCT/US2015/051643 dated Dec. 17, 2015.
International Search Report for PCT App. No. PCT/US2015/051649 dated Dec. 17, 2015.
International Search Report for PCT App. No. PCT/US2015/051646 dated Dec. 18, 2015.
Liu et al., "A novel coral-like porous SnO2 hollow architecture: biomimetic swallowing growth mechanism and enhanced photovoltaic property for dye-sensitized solar cell application", Chem. Commun., vol. 46, pp. 472-474, 2010.
Office Action, Jul. 1, 2011, Office Action dated May 30, 2014.
Final Office Action, Jul. 1, 2011, Final Office Action dated Nov. 13, 2014.
Office Action, Jul. 1, 2011, Office Action dated Jul. 6, 2015.

COMPOSITION CONTAINING SPHERICAL AND CORAL-SHAPED NANOPARTICLES AND METHOD OF MAKING SAME

CROSS-REFERENCE TO RELATED APPLICATIONS

This application claims the benefit of U.S. Provisional Patent Application Ser. No. 62/054,221, filed on Sep. 23, 2014, the disclosure of which is incorporated herein in its entirety.

BACKGROUND

1. Field of the Invention

Disclosed herein are nanoparticle compositions of matter containing spherical nanoparticles and nanoparticles having globular, coral-like shapes and methods of making such compositions.

2. Relevant Technology

The term "nanoparticle" often refers to particles having a largest dimension of less than 100 nm. Nanoparticle research is currently an area of intense scientific interest due to a wide variety of potential applications in biomedical, optical and electronic fields.

Nanoparticles are of great scientific interest as they are, in effect, a bridge between bulk materials and atomic or molecular structures. Bulk materials typically have constant physical properties regardless of size, but at the nano-scale, size-dependent properties are often observed. Thus, properties of materials change as their size approaches the nanoscale and as the percentage of atoms at the surface of a material becomes significant. For bulk materials larger than one micrometer (or micron), the percentage of atoms at the surface is insignificant in relation to the number of atoms in the bulk of the material. The interesting and sometimes unexpected properties of nanoparticles are therefore largely due to the large surface area of the material, which dominates the contributions made by the relatively small bulk of the material.

Nanoparticles often possess unexpected optical properties as they are small enough to confine their electrons and produce quantum effects. For example gold nanoparticles appear deep-red to black in solution. Nanoparticles of yellow gold and grey silicon are red in color. Gold nanoparticles melt at much lower temperatures (~300° C. for 2.5 nm size) than the gold slabs (1064° C.). Absorption of solar radiation is much higher in materials composed of nanoparticles than it is in thin films of continuous sheets of material. In both solar PV and solar thermal applications, controlling the size, shape, and material of the particles, it is possible to control solar absorption.

The size-dependent property changes of nanoparticles include quantum confinement in semiconductor particles, surface plasmon resonance in some metal particles, and superparamagnetism in magnetic materials. Suspensions of nanoparticles are possible since the interaction of the particle surface with the solvent is strong enough to overcome density differences, which otherwise usually result in a material either sinking or floating in a liquid.

The high surface area to volume ratio of nanoparticles provides a tremendous driving force for diffusion, especially at elevated temperatures. Sintering can take place at lower temperatures, over shorter time scales than for larger particles. In theory, this does not affect the density of the final product, though flow difficulties and the tendency of nanoparticles to agglomerate may complicate matters. Moreover, nanoparticles have been found to impart extra properties to various day-to-day products. For example, the presence of titanium dioxide nanoparticles imparts what is called the self-cleaning effect, and, the size being nano-range, the particles cannot be observed. Zinc oxide particles have been found to have superior UV blocking properties compared to its bulk substitute.

Metal, dielectric, and semiconductor nanoparticles have been formed, as well as hybrid structures (e.g., core-shell nanoparticles). Nanoparticles made of semiconducting material may also be labeled quantum dots if they are small enough (typically <10 nm) so that quantization of electronic energy levels occurs. Such nanoscale particles are typically used in biomedical applications as drug carriers or imaging agents.

There are several methods for creating nanoparticles, including both attrition and pyrolysis. In attrition, macro- or micro-scale particles can be ground in a ball mill, a planetary ball mill, or other size-reducing mechanism. The resulting particles are air classified to recover nanoparticles. In pyrolysis, a vaporous precursor (liquid or gas) is forced through an orifice at high pressure and burned. The resulting solid (a version of soot) is air classified to recover oxide particles from by-product gases. Traditional pyrolysis often results in aggregates and agglomerates rather than single primary particles. Ultrasonic nozzle spray pyrolysis (USP) is another method aimed at preventing agglomerates from forming.

A thermal plasma can also deliver the energy necessary to cause vaporization of small micrometer-size particles. The thermal plasma temperatures are in the order of 10,000 K, so that solid powder easily evaporates. Nanoparticles are formed upon cooling while exiting the plasma region. Typical thermal plasma torches used to produce nanoparticles are DC plasma jet, DC arc plasma, and radio frequency (RF) induction plasmas. In the arc plasma reactors, the energy necessary for evaporation and reaction is provided by an electric arc formed between the anode and the cathode. For example, silica sand can be vaporized with an arc plasma at atmospheric pressure. The resulting mixture of plasma gas and silica vapor can be rapidly cooled by quenching with oxygen, thus ensuring the quality of the fumed silica produced.

Scientists have taken to naming their particles after the real-world shapes that they might represent. The terms "nanospheres", "nanoreefs", "nanoboxes" and more have appeared in the literature. These morphologies sometimes arise spontaneously as an effect of a templating or directing agent present in the synthesis, such as miscellar emulsions or anodized alumina pores, or from the innate crystallographic growth patterns of the materials themselves. Some of these morphologies may serve a purpose, such as long carbon nanotubes used to bridge an electrical junction. Others may just serve a scientific curiosity, like the "nanostars."

Amorphous particles usually adopt a spherical shape (due to their microstructural isotropy), whereas the shape of anisotropic microcrystalline whiskers corresponds to their particular crystal habit. At the small end of the size range, nanoparticles are often referred to as clusters. Spheres, rods, fibers, and cups are just a few of the shapes that have been grown.

Nanoparticle characterization is necessary to establish understanding and control of nanoparticle synthesis and applications. Characterization is done by using a variety of different techniques, mainly drawn from materials science. Common techniques are electron microscopy (TEM, SEM), atomic force microscopy (AFM), dynamic light scattering (DLS), x-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, Rutherford backscattering spectrometry (RBS), dual polarisation interferometry, and nuclear magnetic resonance (NMR).

Nanoparticles can be grown into spheres through chemical reduction methods (e.g., silica), while production of spherical nanoparticles from other starting materials has traditionally been through a two-step process. In a first step, growth of nanoparticles from non-silica starting materials by chemical reduction methods produces non-spherical shapes, such as hedrons, platelets, rods, and other non-spherical shapes. While these methods provide good control for size, the resulting non-spherical shapes require further processing before they can become spherical in shape. In a second step, laser ablation is used to aggressively mill the non-spherical particles into quasi-spherical and/or spherical shapes. This process often produces unwanted "scrap" pieces and metal ions as byproduct. The spherical particles are then filtered to remove the ions and unwanted scrap.

Accordingly, there remains a need to manufacture new types of nanoparticles and nanoparticle compositions in order to provide desired properties and/or reduce harmful effects.

SUMMARY

Disclosed herein are nanoparticle compositions comprising: (1) a plurality of spherical-shaped nanoparticles; and (2) a plurality of coral-shaped metal nanoparticles, each coral-shaped metal nanoparticle having a non-uniform cross section and a globular structure formed by multiple, non-linear strands joined together without right angles.

The nanoparticle compositions have utility for various purposes, including, but not limited to, making antimicrobial agents, treating fabrics and other fibrous materials, coatings or treatments for medical devices, conductors of electrical energy, conductors or reflectors of heat energy, reflectors of light energy, catalysts, fuel additives, antioxidants, nucleation sites, oral care products, anti-corrosion formulations, sunscreen compositions, and hemostatic agents, for example. In some embodiments, the coral-shaped metal nanoparticles can advantageously be used together with spherical-shaped metal nanoparticles (e.g., in order to augment, potentiate, or ameliorate desired or undesired effects of spherical-shaped metal nanoparticles).

In some embodiments, the nanoparticle composition can have a mass ratio of spherical-shaped nanoparticles to coral-shaped nanoparticles of about 5:1 to about 20:1, or about 7.5:1 to about 15:1, or about 9:1 to about 11:1 or about 10:1 and/or a particle number ratio of spherical-shaped nanoparticles to coral-shaped nanoparticles of about 50:1 to about 200:1, or about 75:1 to about 150:1, or about 90:1 to about 110:1 or about 100:1.

In some embodiments, the spherical-shaped metal nanoparticles can have a diameter of about 40 nm or less, about 35 nm or less, about 30 nm or less, about 25 nm or less, about 20 nm or less, about 15 nm or less, about 10 nm or less, about 7.5 nm or less, or about 5 nm or less. The spherical-shaped metal nanoparticles can have a particle size distribution wherein at least 99% of the metal nanoparticles have a particle size within 30% of the mean diameter, or within 20% of the mean diameter, or within 10% of the mean diameter and/or wherein at least 99% of the spherical-shaped nanoparticles have a diameter within ±3 nm of the mean diameter, or within ±2 nm of the mean diameter, or within ±1 nm of the mean diameter. The spherical-shaped nanoparticles can have a $\xi$-potential of at least about 10 mV, or at least about 15 mV, or at least about 20 mV, or at least about 25 mV, or at least about 30 mV.

In some embodiments, the coral-shaped metal nanoparticles can have lengths in a range of about 15 nm to about 100 nm, or about 25 nm to about 95 nm, or about 40 nm to about 90 nm, or about 60 nm to about 85 nm, or about 70 nm to about 80 nm. The coral-shaped metal nanoparticles can have a mean length and wherein at least 99% of the coral-shaped metal nanoparticles have a length within about 30% of the mean length, or within about 20% of the mean length, or within about 10% of the mean length. The coral-shaped metal nanoparticles can have a $\xi$-potential of at least about 10 mV, or at least about 15 mV, or at least about 20 mV, or at least about 25 mV, or at least about 30 mV.

In some embodiments, at least a portion of the spherical-shaped and/or coral-shaped nanoparticles can comprises at least one metal selected from the group consisting of gold, platinum, silver, palladium, rhodium, osmium, ruthenium, rhodium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, and alloys thereof. Nanoparticles comprised of silver, gold, and mixtures and alloys thereof can be particularly effective.

In some embodiments, a method of using a nanoparticle composition comprises applying the nanoparticle composition to a substrate and/or exposing a substrate to the nanoparticle composition. The substrate can be a non-living object or a living organism.

In some embodiments, spherical-shaped and/or coral-shaped nanoparticles can be formed by: (1) ablating a target in a heavy atmosphere to form an ejecta plume; and (2) applying an electromagnetic field to the ejecta plume in order to cause the ejecta plume to form the spherical-shaped nanoparticles. In some cases, either spherical-shaped or coral-shaped nanoparticles can be preferentially obtained by altering the distance of electromagnetic field in front of the target. In some cases, spherical-shaped nanoparticles can be preferentially obtained by maintaining the electromagnetic field in a position closer to the target, and coral-shaped nanoparticles can be preferentially obtained by maintaining the electromagnetic field in a position farther from the target.

In some embodiments, a method of manufacturing a one-part nanoparticle composition comprises: (1) obtaining spherical-shaped nanoparticles; (2) obtaining coral-shaped nanoparticles; and (3) combining the spherical-shaped nanoparticles with the coral-shaped nanoparticles to form a one-part nanoparticle composition.

In some embodiments, a method of manufacturing a multi-part nanoparticle composition comprises: (1) obtaining spherical-shaped nanoparticles and storing them in a first part of the multi-part nanoparticle composition; and (2) obtaining coral-shaped nanoparticles and storing them in a second part of the multi-part nanoparticle composition.

These and other advantages and features of the invention will be set forth in part in the description which follows, and in part will become apparent to those skilled in the art upon examination of the following or may be learned by practice of the invention.

DETAILED DESCRIPTION OF THE PREFERRED EMBODIMENTS

Figure 1:
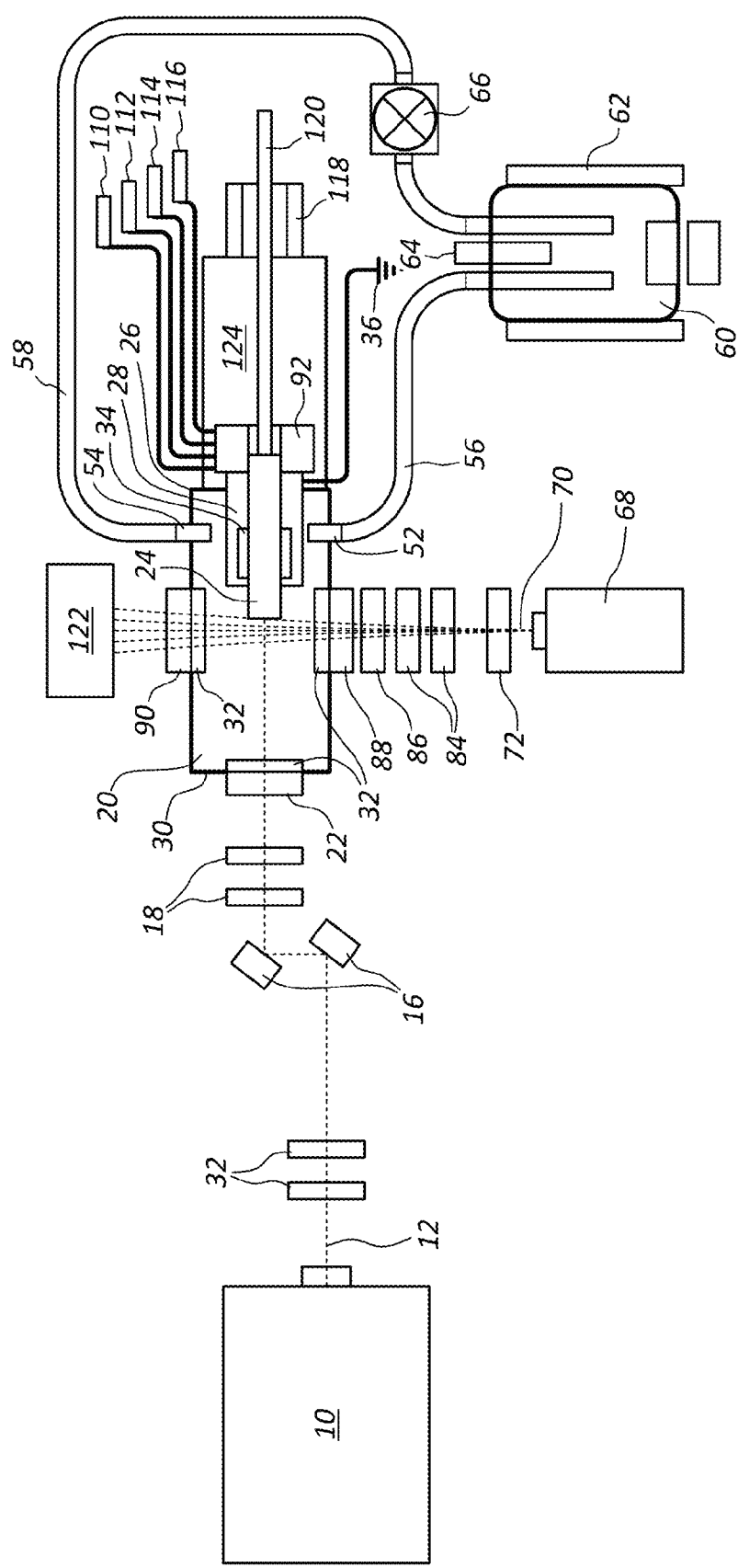
FIG. 1 schematically illustrates a system for making nanoparticles having a desired size and/or shape, including selective or preferential formation of spherical-shaped and coral-shaped nanoparticles.

Disclosed herein are nanoparticle compositions comprising spherical-shaped and coral-shaped metal nanoparticles and methods and systems for selectively or preferentially making spherical-shaped or coral-shaped nanoparticles.

Nanoparticle Configurations

In some embodiments, the metal nanoparticles may comprise or consist essentially of nonionic, ground state metal nanoparticles.

The term "spherical-shaped metal nanoparticles" refers to nanoparticles that are made from one or more metals, preferably nonionic, ground state metals, having only internal bond angles and no external edges or bond angles. In some embodiments, spherical-shaped nanoparticles can have a diameter of about 40 nm or less, about 35 nm or less, about 30 nm or less, about 25 nm or less, about 20 nm or less, about 15 nm or less, about 10 nm or less, about 7.5 nm or less, or about 5 nm or less. Preferably spherical-shaped metal nanoparticles having a solid core. In this way, the spherical nanoparticles are highly resistant to ionization, highly stable, and highly resistance to agglomeration. Such nanoparticles can exhibit a high ξ-potential, which permits the spherical nanoparticles to remain dispersed within a polar solvent without a surfactant, which is a surprising and expected result.

In some embodiments, spherical-shaped nanoparticles can have a particle size distribution such that at least 99% of the nanoparticles have a diameter within 30% of the mean diameter of the nanoparticles, or within 20% of the mean diameter, or within 10% of the mean diameter. In some embodiments, spherical-shaped nanoparticles can have a mean particle size and at least 99% of the nanoparticles have a particle size that is within ±3 nm of the mean diameter, ±2 nm of the mean diameter, or ±1 nm of the mean diameter. In some embodiments, spherical-shaped nanoparticles can have a ξ-potential of at least 10 mV, preferably at least about 15 mV, more preferably at least about 20 mV, even more preferably at least about 25 mV, and most preferably at least about 30 mV.

The term "coral-shaped metal nanoparticles" refers to nanoparticles that are made from one or more metals, such as nonionic, ground state metals having a non-uniform cross section and a globular structure formed by multiple, non-linear strands joined together without right angles. Similar to spherical-shaped nanoparticles, coral-shaped nanoparticles may have only internal bond angles and no external edges or bond angles. In this way, coral-shaped nanoparticles can be highly resistant to ionization, highly stable, and highly resistance to agglomeration. Such coral-shaped nanoparticles can exhibit a high ξ-potential, which permits the coral-shaped nanoparticles to remain dispersed within a polar solvent without a surfactant, which is a surprising and expected result.

In some embodiments, coral-shaped nanoparticles can have a diameter ranging from about 15 nm to about 100 nm, or about 25 nm to about 95 nm, or about 40 nm to about 90 nm, or about 60 nm to about 85 nm, or about 70 nm to about 80 nm. In some embodiments, coral-shaped nanoparticles can have a particle size distribution such that at least 99% of the nanoparticles have a length within 30% of the mean length, or within 20% of the mean length, or within 10% of the mean length. In some embodiments, coral-shaped nanoparticles can have a ξ-potential of at least 10 mV, preferably at least about 15 mV, more preferably at least about 20 mV, even more preferably at least about 25 mV, and most preferably at least about 30 mV.

In general, spherical-shaped metal nanoparticles can be smaller than coral-shaped metal nanoparticles and in this way can provide very high surface area for catalyzing desired reactions or providing other desired benefits. On the other hand, the generally larger coral-shaped nanoparticles can exhibit higher surface area per unit mass compared to spherical-shaped nanoparticles because coral-shaped nanoparticles have internal spaces and surfaces rather than a solid core and only an external surface. In some cases, providing compositions containing both spherical-shaped and coral-shaped nanoparticles can provide synergistic results. For example, coral-shaped nanoparticles can help carry and/or potentiate the activity of spherical-shaped nanoparticles in addition to providing their own unique benefits.

In some embodiments, the mass ratio of spherical-shaped nanoparticles to coral-shaped nanoparticles in the nanoparticle composition can be in a range of about 1:1 to about 50:1, or about 2.5:1 to about 25:1, or about 5:1 to about 20:1, or about 7.5:1 to about 15:1, or about 9:1 to about 11:1, or about 10:1. The particle number ratio of spherical-shaped nanoparticles to coral-shaped nanoparticles in the nanoparticle composition can be in a range of about 10:1 to about 500:1, or about 25:1 to about 250:1, or about 50:1 to about 200:1, or about 75:1 to about 150:1, or about 90:1 to about 110:1, or about 100:1, The nanoparticles, including spherical-shaped and coral-shaped nanoparticles, may comprise any desired metal, mixture of metals, or metal alloy, including at least one of silver, gold, platinum, palladium, rhodium, osmium, ruthenium, rhodium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, or alloys thereof According to some embodiments, the nanoparticles will comprise at least one of silver or gold. Due to the nature of silver and gold atoms making up the nanoparticles, it has been found that gold nanoparticles are better able to hold together at very small sizes (e.g., smaller than about 5-7 nm) compared to silver nanoparticles. On the other hand, a gold-silver alloy provides the particle stabilizing activity of gold and the higher antimicrobial activity or other desired properties of silver.

Examples of methods and systems for manufacturing spherical-shaped nanoparticles are disclosed in U.S. Pat. Pub. No. 2013/0001833 to William Niedermeyer (the "Niedermeyer Publication"), which is incorporated herein by this reference in its entirety.

Examples of methods and systems for manufacturing coral-shaped nanoparticles are disclosed in U.S. Provisional Application No. 62/054,126, filed Sep. 23, 2104, in the name of William Niedermeyer (the "Niedermeyer Application"), which is incorporated herein by this reference in its entirety.

Production Apparatus and Methods

In some embodiments, coral-shaped metal nanoparticles, rather than spherical nanoparticles, can be selectively manufactured by repositioning an electromagnetic field at a given energy density to a distance that is farther away from the metal surface being ablated. In some embodiments, moving an electromagnetic field at a given energy density farther away from the metal surface being ablated provides a smaller effect on the nanoparticles in the ejecta plume so as to not force them into a spherical shape.

FIG. 1 schematically illustrates an embodiment of an apparatus for use in a method or system for making metal nanoparticles and which can be configured and operated to selectively or preferentially make spherical-shaped or coral-shaped metal nanoparticles. FIG. 1 more particularly depicts a primary laser 10 configured to emit or deliver discrete energy packets of photon energy 12 in a pulsed manner. Typically, the diameter of pulsed emission 12 exiting primary laser 10 can be expanded through beam-expanding optics 14 to reduce its power density and allow pulsed emission 12 to move through scanning optics 16 without destroying optic coatings. After leaving scanning optics 16, pulsed emission 12 then typically passes through beam collimating optics 18 to create a desired spot size for pulsed emission 12 as it enters a chamber 20 through an optic window 22 and interacts with a target 24 (e.g., metal or metal alloy).

Scanning optics 16 can slightly adjust the direction of each pulse of emission 12 to move pulsed emission 12 around the surface of target 24 and are typically either polar or x-y scanners. This precludes pulsed emission 12 from repeatedly striking the exact same location on target 24, thereby allowing for optimal particle ablation during each pulse and efficiently utilizing target 24. Significantly, whether target 24 moves or pulsed emission 12 moves is less important than precluding repeated energy delivery to the same point on target 24. Further, one skilled in the art will recognize that the path of pulsed emission 12 preferably occurs within a hermetically sealed environment to preserve the integrity of laser beam profile (typically either a "top hat" or Gaussian profile).

The type and frequency of primary laser 10 is primarily a function of the target material to be ablated, commercial availability, and/or cost. Typically the target material of target 24 will have known wavelength absorption bands. Where no known wavelength absorption bands exists for a given target material, or where further optimization from reported values is desired, the frequency for primary laser 10 can be experimentally determined by finding a suitable and strong absorption band for the specific material to be ablated.

Further, the beam spot size and energy density will control the total energy delivered ($E_T$) in each energy packet or pulse for emission 12. This will be a function both of the target material's bonding energy ($E_B$) as well as the number of total atoms/molecules to be contained within the desired final spherical nanoparticle. According to some embodiments, the total energy delivered ($E_T$) in each energy packet or pulse for emission 12 can be increased when making coral-shaped metal nanoparticles as compared to spherical-shaped metal nanoparticles.

The duration for pulsed emission 12 is selected to preferably allow delivery of sufficient energy within each pulse or energy packet to ablate the target material of target 24, while still maintaining energy content of the pulse below the ionization energy of the target. This maximum pulse duration (PD) is particularly significant in the case of metallic targets and again can be determined experimentally or by dividing the target ionization energy ($E_I$—in joules) by the total energy delivered from emission 12 ($E_T$—in joules/sec) as shown by the following equation:

$$PD = E_I/E_T$$

By way of example, typically for preparation of spherical-shaped silver (Ag) nanoparticles with diameters less than 35 nm the pulse duration (PD) for creation of a suitable ejecta event has been found to be less than 10 nanoseconds. In order to create coral-shaped metal nanoparticles, such as gold nanoparticles, the pulse duration (PD) can be less than 1 microsecond and greater than 5 nanoseconds. In general, longer pulses yield larger particles, and shorter pulses yield smaller particles.

The profile of the laser beam can be selected to provide the most efficient transfer of photonic energy to phonon energy within the target, such as the well-known "top hat" or "Gaussian" profiles, and can be further tuned to deliver photonic energy packets of a specific time duration within an overall controlled area for an energy density that induces specific ejecta event shape, size, and density of ejecta material.

As further illustrated in FIG. 1, target 24 is preferably held within a back end 26 of hollow reactor chamber 20 by a target holder 28. A front end 30 of chamber 20 contains optic window 22, which permits passage of pulsed emission 12 therethrough on its way to target 24. Preferably, a small piezo-electrically controlled vibrator 32 can be mounted inside front end 30 of chamber 20 behind optic window 22 such that its regular vibration precludes buildup of nanoparticles on it, thereby protecting optic window 22. If nanoparticle buildup occurs on optic window 22, the propensity for damage by the incoming laser emission may increase. The hollow interior of chamber 20 acts to contain the ejecta event (not shown) as the ejecta plume leaves the surface of target 24 after being impacted by each pulse of emission 12.

When a pulse from emission 12 interacts with the surface of target 24, the energy of the laser photons transfers into the lattice structure of the target, becoming phonon energy, which breaks the intranuclear bonds within the lattice structure and releases particles from the target surface. Because the bonding energies between the atoms within the lattice structure control the quantity of material that is ablated by a specific quantity of energy delivered to the target surface, lower bonding energies between atoms result in more rapid target material ablation. In some embodiments, processes to "soften" a target, such as annealing, are utilized to increase the rate of a target's ablation. In some embodiments, target 24 can be heated by a target heater 34, which will typically increase the temperature of target 24 by approximately 10° C., for example, above ambient conditions to further decrease the bonding energies within the target's lattice structure.

Despite attempts to control the energy delivered to the target surface to cause formation of specifically sized particles as discussed above, the particles of an ejecta event may contain a distribution of uncharged, nonionic particles ranging in size from small clusters of single digit atoms/molecules to particles of the generally desired size as well as many even larger particles. Further, in the case of metallic targets, even with laser energy delivered to the target being less than the target's ionization energy, the initial ejecta event will likely also contain some ionized, individual atoms. As such, metallic targets are preferably charged as an anode and grounded through an electrical outlet 36 so that ablated ionized atoms are electrostatically drawn back into target 24 and reabsorbed into the target material's crystalline structure, thereby eliminating or minimizing free ions in the ejecta event and in subsequently produced nanoparticles.

In order to facilitate continuous production and removal of the ablated particles, chamber 20 can contain a fluid input port 52 and a fluid output port 54, which are connected through input 56 and output 58 tubing or piping or other similar structures to a tank 60 or other similar holding vessel or chamber that contains the desired fluid, whether liquid or gas or other heavy atmosphere. The temperature of the fluid within tank 60 can be controlled through the use of a heating jacket 62 or other known mechanisms and preferably contains a mechanism for mixing the fluid, whether by stirring or other mechanism. In systems utilizing liquids, the pressure within the chamber can be controlled by adjusting the height of the output port 54. The pressure in gas systems can be controlled by controlling the gas pressure. Similarly, in vacuum systems, the creation and maintenance of the vacuum within the system will operate with commonly understood components. Tank 60 can further include a sample port 64 which could also include sensors for temperature, pressure and/or fluid volume, for example. Further, one skilled in the art will recognize and understand that all material surfaces within the chamber, input and output ports, tubing or piping and tanks are advantageously nonreactive, non-attractive and non-absorbent to or with the specific nanoparticles being created. For example, untreated glass and quartz can readily absorb many types of nanoparticles, particularly metallic particles, and can pose substantial problems for use as materials for the reaction chamber 20. Preferred materials therefore include relatively insert substances, such as teflon, PEEK, and PET. Further, where a pump 66 is needed for a liquid system, peristaltic pumps are preferred.

Fluid flow rate can be maintained at low linear velocities above target 24 to provide laminar flow through reaction chamber 20 so as to allow the particles within the ejecta event to interact with the gradient electromagnetic field(s) without interference from the fluid flow. Additionally, by minimizing the distance between target 24 and front 30 of reaction chamber 20, the volume of solution in front of target 24 through which emission 12 passes will be minimized. Over time, the quantity of uniformly sized nanoparticles that have passed through the gradient electromagnetic field(s) will increase within the fluid. Since emission 12 must pass through this fluid above target 24, emission 12 has the capacity to further split the particles contained within the fluid. By minimizing the volume above target 24, the quantity of particles that can potentially interact with emission 12 can be reduced and as such, continued destruction of the particles by the ongoing laser energy can be minimized.

The energy packets delivered to target 24 and the target material's bonding energies will be the primary control factors for the initial particle size distribution within the ejecta event, which initial particle size distribution can influence the size of particles ultimately produced. To produce larger coral-shaped nanoparticles instead of smaller spherical-shaped nanoparticles, for example, the energy density of packets delivered to target 24 can be increased for a particular metal being ablated.

Figure 2:
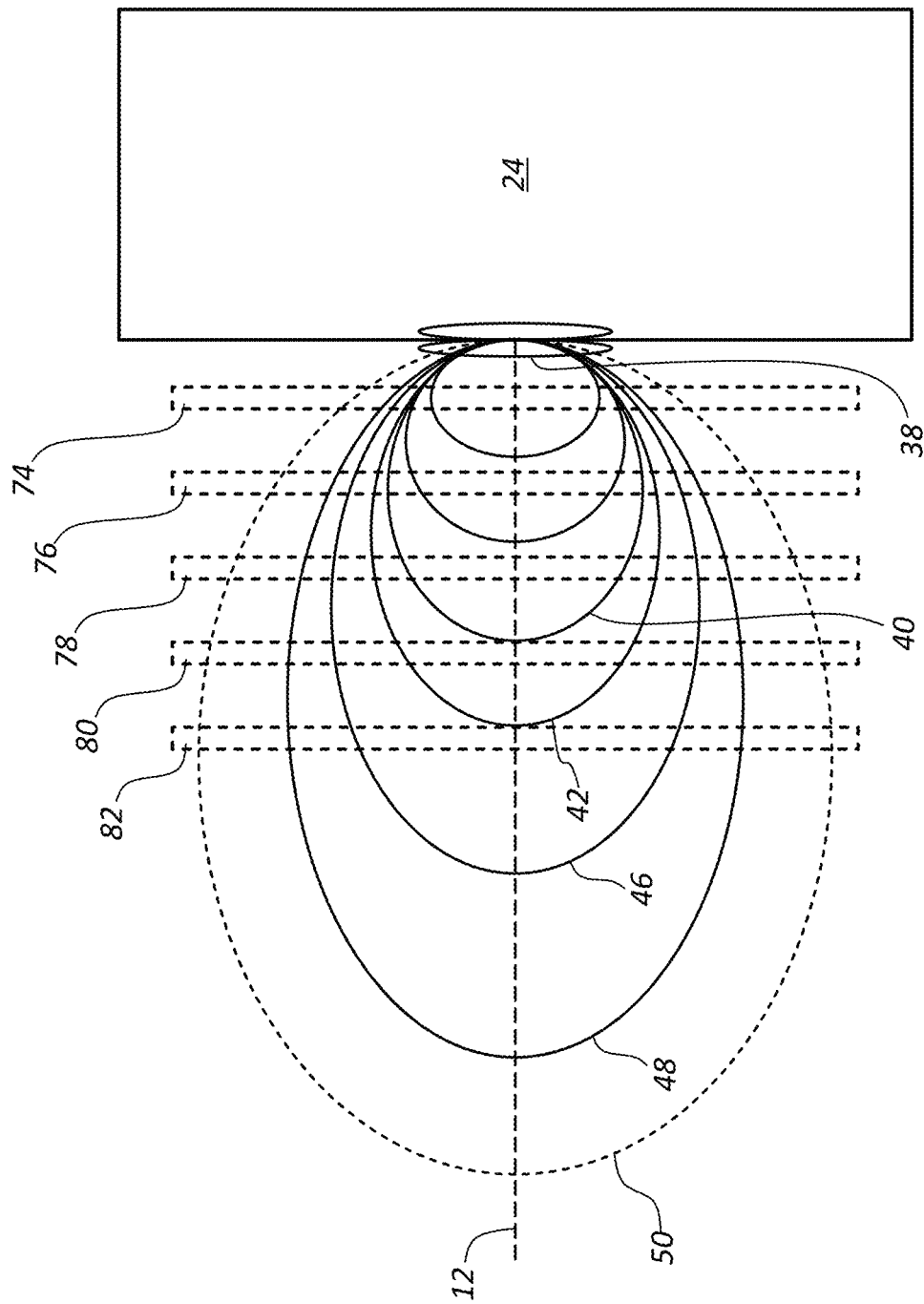
FIG. 2 schematically illustrates an ejecta plume within a heavy atmosphere or liquid moving away from a target surface and its interaction with multiple gradient electromagnetic fields.

FIG. 2 illustrates the behavior of ablated particles within an ejecta plume within a heavy atmosphere as they leave the surface of target 24 (i.e., not in a vacuum system, which would produce an ejecta spray rather than an ejecta plume). In this embodiment which utilizes a heavy atmosphere, as pulsed emission 12 interacts with target 24, the ablated particles form an initial ejecta plume containing discrete ejecta material within a Knudsen boundary layer 38 (which boundary layer would not exist in a vacuum system). This Knudsen boundary layer then proceeds to expand away from the surface of target 24 over time as shown by the successive boundary layers 40, 42, 44, 46, 48 until the ejecta plume loses all definition and the Knudsen boundary layer no longer exists at location 50.

According to some embodiments, laser ablation of a metal target surface (e.g., silver) can be performed by a Nd-YAG laser at 1064 nm wavelength using 3.9 nanosecond pluses to deliver approximately 500 mJ energy per pulse. By way of comparison, without the use of any gradient electromagnetic fields, the energy content of the laser created an average particle size of 23.15 nm, with 99+% of the particles being within ±14.2 nm. To provide greater uniformity shape and stability of the nanoparticles and impart increased $\xi$-potential to the particles ablated from the surface of target 24, the system utilizes an electromagnetic field, such as multiple electromagnetic fields that are substantially parallel to the surface of target 24. In the embodiment shown in FIG. 1, a set of multiple electromagnetic fields are produced by a secondary laser 68 that emits a secondary laser beam 70. While the embodiment of FIG. 1 utilizes a laser to create the electromagnetic field(s), it is understood that multiple other sources of electromagnetic energy, such as sources of microwave energy, can be used.

Figure 3:
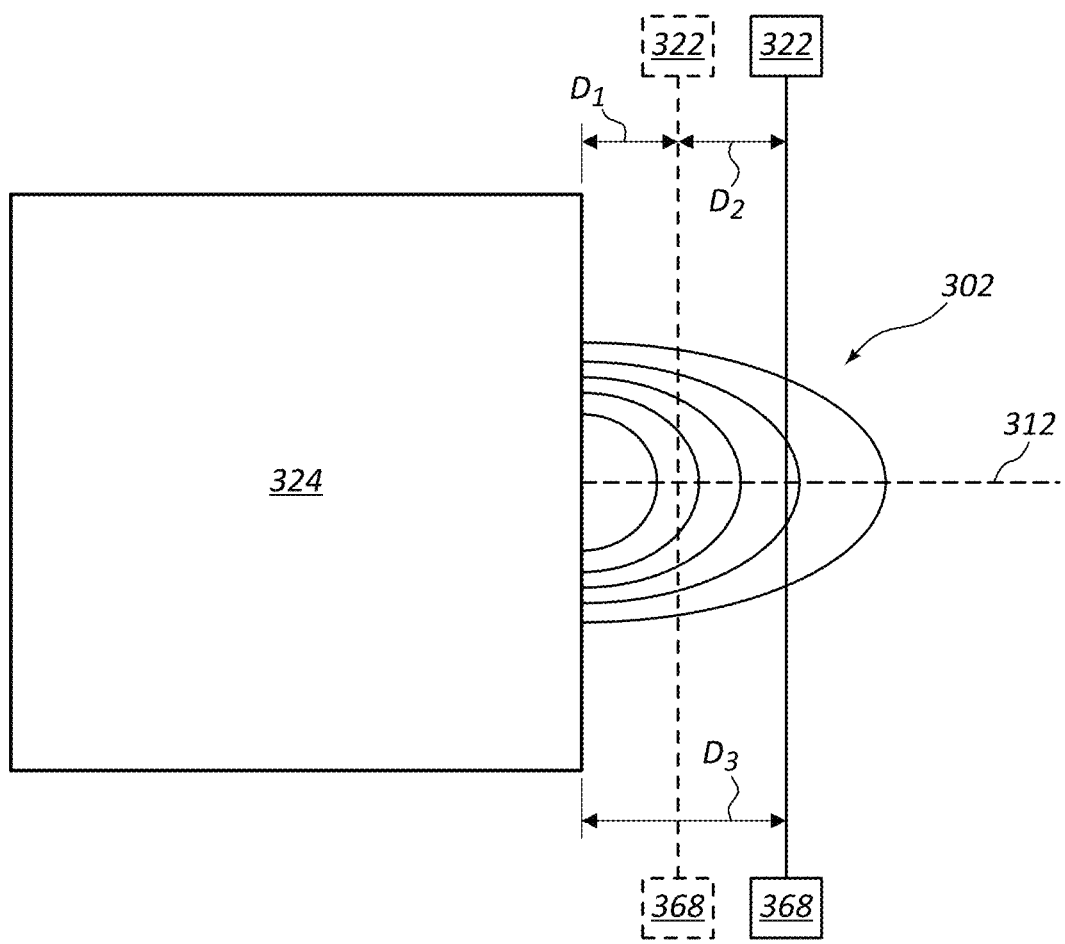
FIG. 3 schematically illustrates positioning one or more electromagnetic fields at a distance in from of the metal target surface in order to selectively produce nanoparticles of a desired size and/or shape, including selectively or preferentially producing either spherical-shaped or coral-shaped metal nanoparticles.

FIG. 3 schematically illustrates how an apparatus (as in the Niedermeyer Publication) configured to produce spherical-shaped metal nanoparticles can be modified to produce coral-shaped metal nanoparticles.

As illustrated in FIG. 3, in a first configuration for producing spherical-shaped metal nanoparticles using apparatus as disclosed herein, a secondary laser 368 and optional detector 322 is/are positioned at a first distance $D_1$ in front of the surface of a metal surface or target 324 being ablated by a pulsed emission 312 to form an ejecta plume 302. In order to selectively produce coral-shaped metal nanoparticles instead of spherical-shaped metal nanoparticles, secondary laser 368 can be positioned at or repositioned to a second distance $D_3$ in front of the surface of metal surface or target 324 being ablated by pulsed emission 312 (e.g., by moving or repositioning secondary laser 368 and optional detector 322 an additional distance $D_2$ beyond first distance $D_1$). Moving the secondary laser 368 (and optional detector 322) can be performed using any position adjustment means known in the art, including, but not limited to, one or more of electric motors, gears, pulleys, cables, rods, screws, set screws, knobs, rails, slots, magnets, and the like. A caliper, laser, or other distance measuring means can be used to determine and/or set an appropriate or desired distance of the secondary laser 368 in front of metal surface or target 324.

According to some embodiments, the energy density of one or more electromagnetic fields positioned in front of the surface of target 324 can remain the same in order to prevent ionization while maintaining desired nanoparticle manipulation forces. However, it has now been found that when the one or more electromagnetic fields are positioned further away from the surface of target 324 (e.g., by second distance $D_3$), it/they can have a smaller effect on the nanoparticles in the ejecta plume so as to reduce or minimize the forces required to force or cause the nanoparticles to form spherical nanoparticles. Instead, coral-shaped metal nanoparticles can be formed by selecting an appropriate distance of electromagnetic fields in front of the metal target surface.

By way of example, when an apparatus as illustrated in FIG. 1 is configured to make spherical-shaped metal nanoparticles, such as according to methods disclosed in the Niedermeyer Publication, the at least one electromagnetic field can be positioned at a distance of about 0.5 mm to about 1.5 mm, or about 0.75 mm to about 1.25 nm, or about 0.95 mm to about 1.05 mm in front of the metal surface being ablated so as to manipulate the ejecta plume and form spherical-shaped metal nanoparticles having a particle size of 40 nm or less, 35 nm or less, 30 nm or less, 25 nm or less, 20 nm or less, 15 nm or less, 10 nm or less, 7.5 nm or less, or 5 nm or less. The spherical-shaped metal nanoparticles can have a particle size distribution wherein at least 99% of the metal nanoparticles have a particle size within 30% of the mean diameter, or within 20% of the mean diameter, or within 10% of the mean diameter and/or wherein at least 99% of the spherical-shaped nanoparticles have a diameter within ±3 nm of the mean diameter, or within ±2 nm of the mean diameter, or within ±1 nm of the mean diameter. The spherical-shaped nanoparticles can have a $\xi$-potential of at least about 10 mV, or at least about 15 mV, or at least about 20 mV, or at least about 25 mV, or at least about 30 mV By comparison, when an apparatus as illustrated in FIG. 1 is configured to make coral-shaped metal nanoparticles as disclosed herein, the at least one electromagnetic field can be positioned at a distance of about 1.5 mm to about 5 mm, or about 2 mm to about 4 nm, or about 2.5 to about 3.5 mm in front of the metal surface being ablated so as to manipulate the ejecta plume and form coral-shaped metal nanoparticles having a particle size of about 15 nm to about 100 nm, or about 25 nm to about 95 nm, or about 40 nm to about 90 nm, or about 60 nm to about 85 nm, or about 70 nm to about 80 nm. The coral-shaped metal nanoparticles can have a mean length and wherein at least 99% of the coral-shaped metal nanoparticles have a length within about 30% of the mean length, or within about 20% of the mean length, or within about 10% of the mean length. The coral-shaped metal nanoparticles can have a $\xi$-potential of at least about 10 mV, or at least about 15 mV, or at least about 20 mV, or at least about 25 mV, or at least about 30 mV. The ability to form coral-shaped metal nanoparticles having controlled sizes and/or a narrow particle size distribution is a surprising and unexpected result, particularly since the particles are not being forced into a uniform, spherical configuration.

In general, while the initial acceleration of nanoparticles leaving target 24 can typically reach velocities at or near sonic speed, the particle accelerations can be controlled though the use of pressure within the reaction chamber. This means that in a vacuum the near sonic speed will not be substantially diminished as the nanoparticles move toward and ultimately deposit onto the front end 30 of the chamber 20. However, where either gas or liquid media are used to manipulate nanoparticle flow, the pressure within reaction chamber 20 can be modified to have an effect on the rate of accelerations in the ejecta plume, thereby providing the particles with greater or lesser time to be affected by the electromagnetic field(s) created by secondary laser emission 70. Again, such variables can be modified to yield coral-shaped metal nanoparticles of desired size and/or shape.

According to some embodiments, the energy density of pulsed emission 312 can remain the same or, alternatively, it can be increased in order to increase the rate of ablation and/or to create larger metal nanoparticles within ejecta plume 302. This can yield coral-shaped nanoparticles of larger size compared to when using a pulsed emission 312 with lower energy density.

Returning to FIGS. 1 and 2, prior to secondary emission 70 passing into reactor chamber, this beam can pass through a holographic diffraction grating optic 72 that produces five identifiable and discrete beams of differing spatial orders and different energies 74, 76, 78, 80 and 82 that can act as discrete electromagnetic fields. While five discrete beams are shown in FIG. 2, the number of such beams may be greater than five or less than five (e.g., three). The holographic diffraction grating optic 72 will preferably allow at least 95% of the energy of secondary emission 70 to pass through. Of course, rather than utilize a diffraction grating optic to create multiple discrete laser emissions or fields from a single source laser emission, multiple individual lasers could be utilized to achieve the same effect. The frequency and intensity of these electromagnetic fields can be correlated between the absorption bands of the target material and the plasmon resonance of the ultimately desired sized spherical nanoparticle. Typically the frequency of secondary laser emission 70 will be in the range of multiples of the frequency of the primary laser emission 12. The frequency is preferably a frequency that is absorbed by the target material, but is absorbed less by the material once it has been ablated and forms the desired particle size and shape, which should be a factor of the plasmon resonance of the ultimately desired sized nanoparticle.

Further, a minimum energy density of the discrete electromagnetic fields 74, 76, 78, 80 and 82 may be advantageous to cause manipulation of the nanoparticles caused by the ejecta event, as opposed for example to mere observation of the ejecta event. This manipulation has the effect of imparting sufficient energy to the nanoparticles that will cause mis-sized particles, i.e., particles that are either larger or smaller than desired, to either lose mass (in the case of nanoparticles that are too large) or gain mass (in the case of nanoparticles that are too small) as well as cause the nanoparticles to adopt a uniform shape. It is believed that this effect occurs because mis-sized particles will more readily absorb the energy of a discrete electromagnetic field of a specific frequency than the desired-sized particles. Because the desired-sized particles absorb little energy from the electromagnetic field, little impetus exists for these particles to change size or shape as they move through the electromagnetic field. Conversely, because mis-sized particles will absorb the energy from the electromagnetic field, the resulting vibrational and/or motion state of these particles creates an impetus for these mis-sized particles to gain or lose material so as to conform to a size and shape that is in harmony with the electromagnetic field.

This determination of the energy density of an electromagnetic field can begin by estimating the mass of all particles within the ejecta event (the mass of a single ejecta event can be determined by weighing the target before and after ablation and calculating the mass loss per ejecta event). Additionally, the mass of the size and shape of the ultimately desired nanoparticles is also known.

When utilizing a laser method to create the discrete electromagnetic fields, the energy of photons at the given frequency is known. Therefore, a minimum quantity of photons that are necessary to cause change in a single particle to a desired size and shape can be determined experimentally. The more mass within the ejecta event, the higher required energy density of any one of the discrete electromagnetic fields. Further, the maximum energy density of any one of the discrete electromagnetic fields will preferably be less than the ionization energy of the material (e.g., metal) of the desired sized nanoparticles. Once the energy densities of each of the electromagnetic fields is known, then the total energy density of secondary beam 70, which is used to create the multiple discrete electromagnetic fields, will likewise be known.

Again, as shown in FIG. 1, after passing through diffraction grating optic 72, the now five discrete laser emissions then preferably pass through intensifying optics 84, such as collimating lenses, which ensure that the maximum amount of energy is applied to the nanoparticles in the ejecta plume. The discrete laser emissions then pass through a cylindrical lens 86, which takes the discrete linear laser emissions and turns them into discrete planar laser emissions that then pass into chamber 20 through an input optic window 88 and then in front of target 24 and ultimately out the opposite side of chamber 20 through an output optic window 90. One of skill in the art will understand that the optics may include coatings and/or other properties that reduce losses in a laser emission frequency. Further, the optics may be advantageously able to withstand degradation by the power of the laser emission. Additionally, input and output optics 88 and 90, respectively, may each advantageously have a piezoelectrically controlled vibrator 32 that can be mounted inside chamber 30 behind both optics such that regular vibration of the optics will preclude buildup of particles, thereby protecting the optics from particle buildup and subsequent degradation by secondary laser emissions.

As can be seen in FIG. 2 the discrete fields can be generally parallel to target 24 and perpendicular to primary laser emission 12 such that if laser emission 12 is designated as an x-axis, each of the discrete fields from emission(s) 70 form a y-z plane in front of target 24. Depending on the exact specification of holographic diffraction grating optic 72, the spatial orders of the discrete laser emissions of the fields can be ordered. The laser emission fields closest and farthest from target 24, i.e., fields 74 and 82, respectively, can have identical energy densities, as can the fields adjacent to the center, i.e., fields 76 and 80. The center field, i.e., field 78, can be of a different energy density from the other two sets of fields. In one example, outer fields 74 and 82 can have the lowest density, fields 76 and 80 can have higher energy density, and center field 78 can have the highest energy density. In another example, outer fields 74 and 82 can have the highest density, fields 76 and 80 can have relatively lower energy density, and center field 78 can have the lowest energy density. Ideally, the closest electromagnetic field 74 is at or near the target surface 24 such that the effect of the field on the particles is nearly instantaneous. At a minimum, it is preferred that first electromagnetic field 74 act on the ejecta plume before the Knudsen boundary layer dissipates.

When configured to produce spherical-shaped nanoparticles, nanoparticles within the ejecta plume that have passed through this series of electromagnetic fields are observed to possess relative uniformity of shape and size, with >99% of the spherical particles being within ±3 nm, ±2 nm, or ±1 nm having been achieved. Furthermore, such a process can also impart a high $\xi$-potential to spherical nanoparticles, which greatly inhibits or prevents agglomeration and yields particles that can remain dispersed in a polar liquid without a surfactant. In some embodiments, the spherical-shaped metal nanoparticles can have a $\xi$-potential greater than 10 mV, preferably greater than about 15 mV, more preferably greater than about 20 mV, even more preferably greater than about 25 mV, and most preferably greater than about 30 mV.

Alternatively, when reconfigured to produce coral-shaped nanoparticles, nanoparticles within the ejecta plume that have passed through this series of electromagnetic fields are observed to possess relative uniformity of size, but not necessarily shape, as illustrated in FIGS. 4A-4E. Nevertheless, such a process can yield coral nanoparticles with no right angles and therefore no external edge or external bond angles. Similar to spherical-shaped particles, coral-shaped nanoparticles can have only interior bond angles, which greatly inhibits or prevents ionization. In some embodiments, the "coral-shaped metal nanoparticles" can have a $\xi$-potential greater than 10 mV, preferably greater than about 15 mV, more preferably greater than about 20 mV, even more preferably greater than about 25 mV, and most preferably greater than about 30 mV.

The disclosed apparatus is not limited to the use of five electromagnetic fields created from a holographic diffraction grating optic. For example, where only three electromagnetic fields are utilized in place of the five fields of the above embodiment, one might expect less size uniformity as well as lower $\xi$-potential. Where a single electromagnetic field is used in place of the five fields of the above embodiment, one would expect size uniformity and/or shape to increase compared to a system without any electromagnetic field, but less than multiple electromagnetic fields. In some embodiments, the disclosed apparatus includes more than five electromagnetic fields. In some embodiments, the disclosed apparatus includes less than five electromagnetic fields (e.g., one to four electromagnetic fields).

Figure 4:
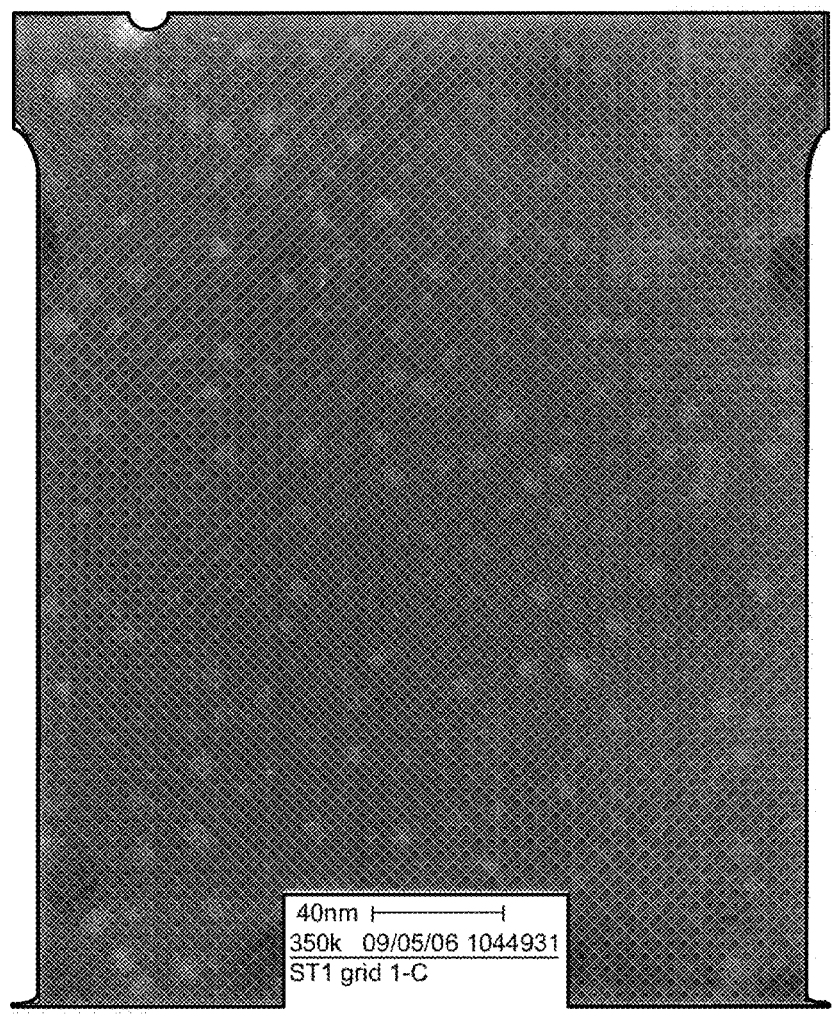
FIG. 4 is a transmission electron microscope image (TEM) of exemplary spherical-shaped metal nanoparticles having substantially uniform size and narrow particle size distribution for use in making nanoparticle compositions.
Figure 5A:
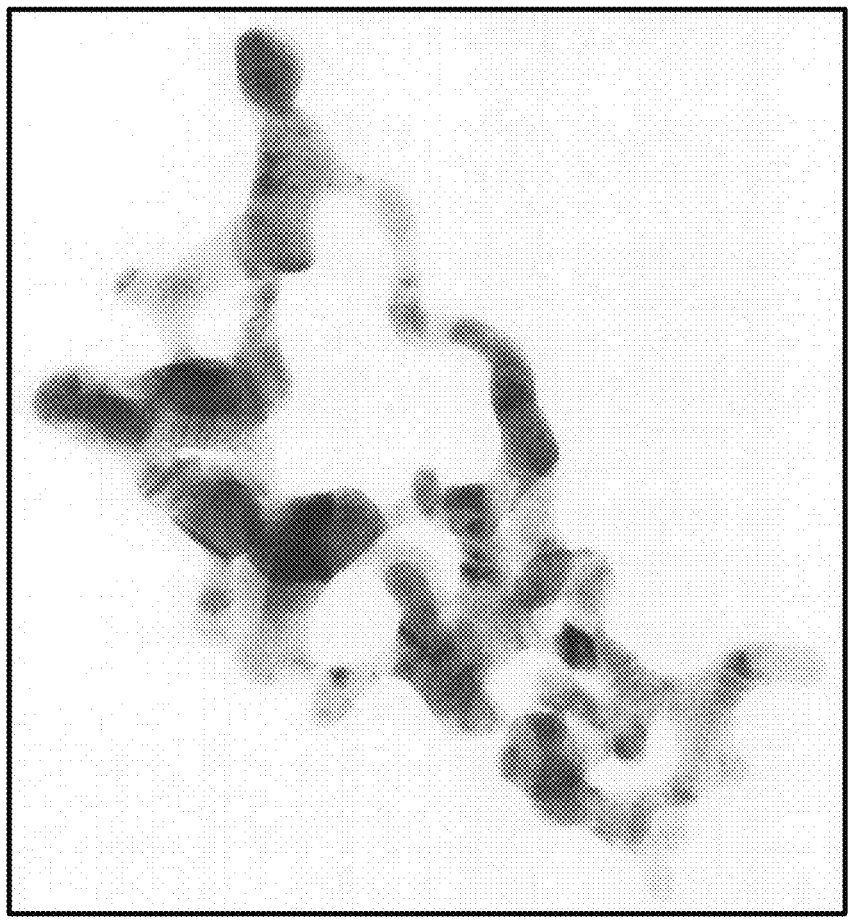
FIGS. 5A-5E are transmission electron microscope images (TEMs) of exemplary coral-shaped metal nanoparticles for use in making nanoparticle compositions.
Figure 5B:
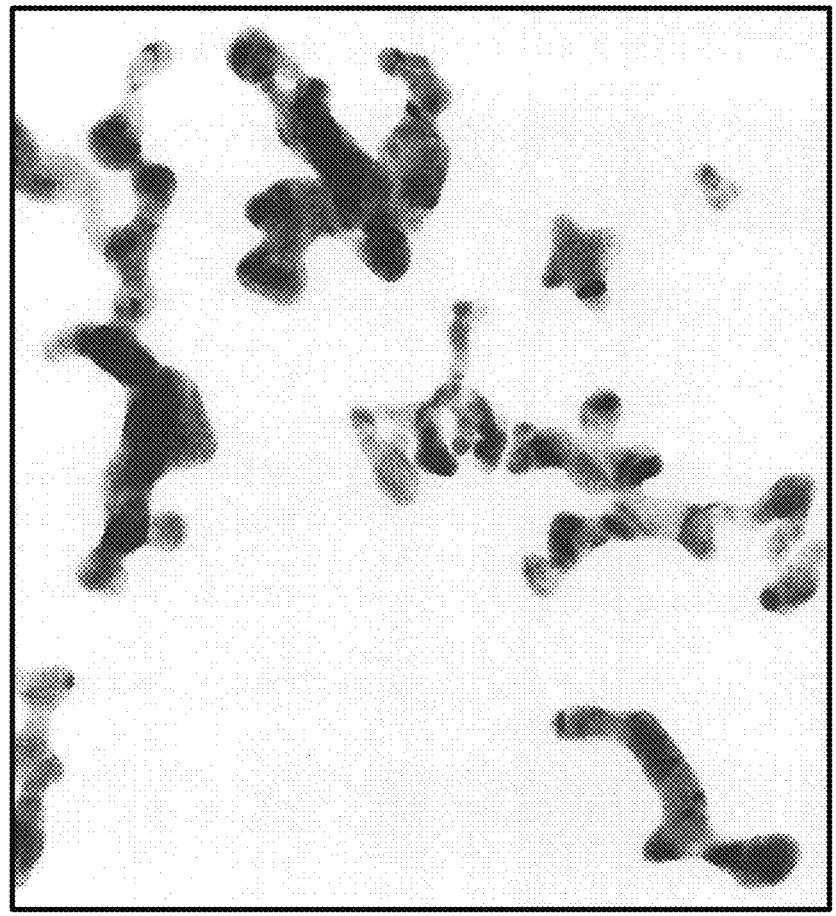
Figure 5C:
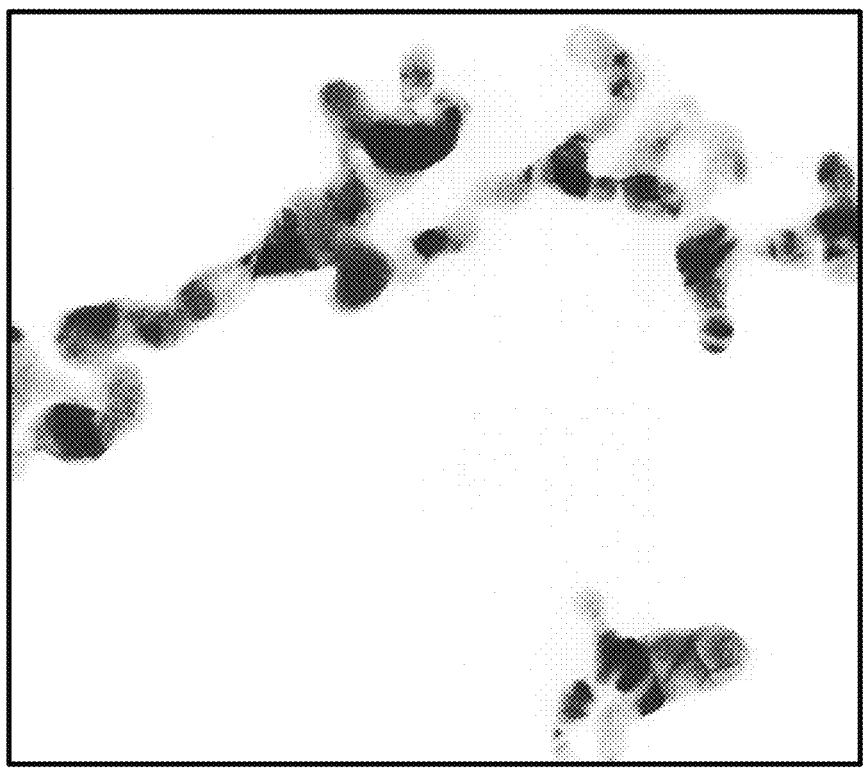
Figure 5D:
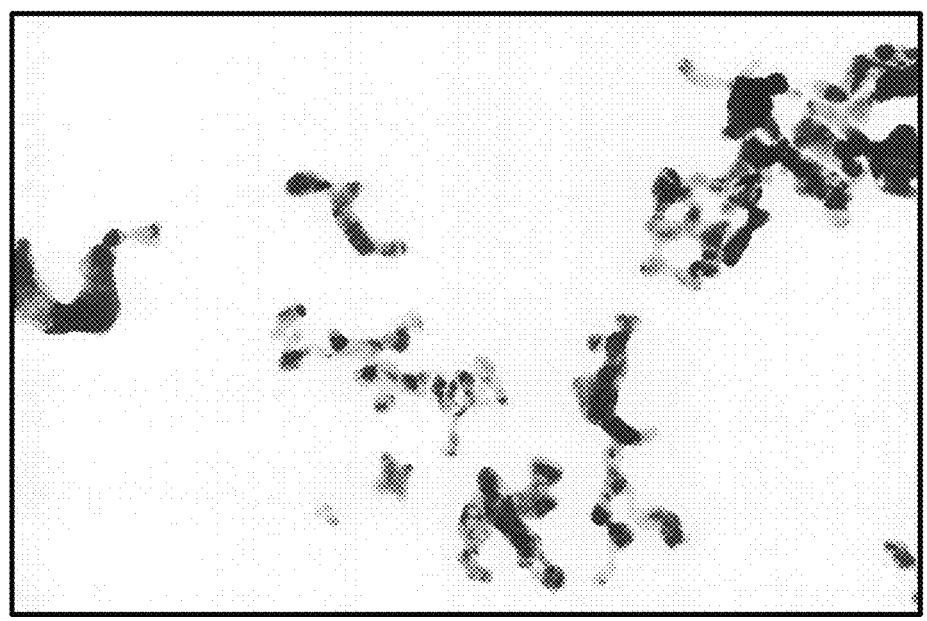
Figure 5E:
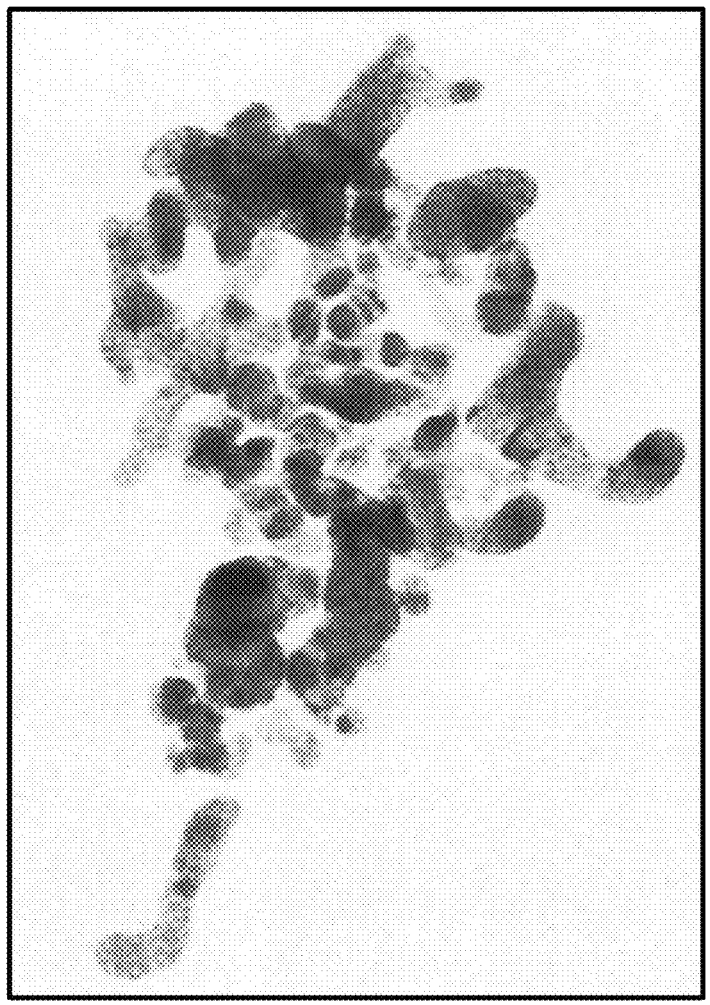

FIG. 4 is a transmission electron microscope image (TEM) of exemplary spherical-shaped nanoparticles. The illustrated nanoparticles are spherical-shaped silver (Ag) nanoparticles of substantially uniform size, with a mean diameter of about 10 nm and a narrow particle size distribution. In some embodiments, spherical-shaped nanoparticles can have a solid core rather than being hollow, as is the case with conventional metal nanoparticles, which are usually formed on the surfaces of non-metallic seed nanoparticles (e.g., silica), which are thereafter removed to yield hollow nanospheres.

FIGS. 5A-5E are transmission electron microscope images (TEMs) of exemplary coral-shaped metal nanoparticles having non-uniform, asymmetrical cross sections and globular structures formed by multiple, non-linear strands joined together without right angles. The illustrated nanoparticles are coral-shaped gold nanoparticles. In many cases, the coral-shaped nanoparticles include non-uniformly and asymmetrically shaped strands, some of which form closed loop structures with no free ends and some of which form strands or branches. In most cases, it appears the non-uniformly shaped strands have an essentially non-linear configuration with no right angles. The diameters of the non-uniformly and asymmetrically shaped strands can also vary along their length. Multiple closed loop structures and/or strands can be joined together, typically in a non-uniform, asymmetrical fashion.

Figure 6:
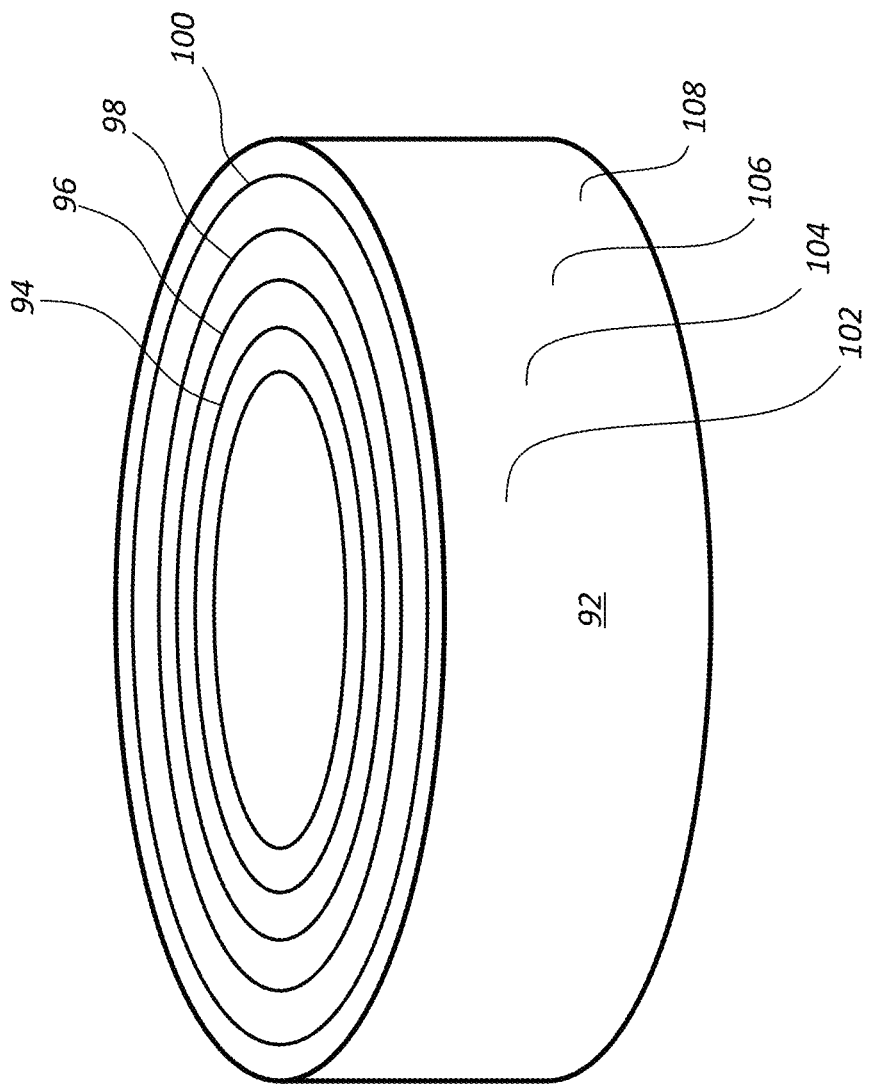
FIG. 6 schematically illustrates a toroid containing multiple concentric bands on its surface.

In some embodiments, a ceramic (or other nonmetallic) toroid 92 can be mounted around target 24. As shown in FIG. 6, a top side of toroid 92 can have multiple metallic concentric bands 94, 96, 98, and 100 disposed on the surface of toroid 92. Concentric metallic bands 94, 96, 98, and 100 can be connected to electric leads 102, 104, 106, and 108, respectively. Electric leads 102, 104, 106, and 108 can each be connected to individual high voltage power suppliers 110, 112, 114, and 116 (shown in FIG. 1), which can produce a gradient electric field around and in front of target 24. In preferred embodiments, this gradient electric field is used in addition to, and not in replacement of, the electromagnetic field(s) discussed above. The gradient electric field can be used to manipulate accelerations and movement of nanoparticles within chamber 20. The gradient field can be controllable by changing voltages on metallic concentric bands 94, 96, 98, and 100. For example, in a vacuum process, nanoparticle movement can be controlled by the gradient electric field.

In some embodiments, one or more additional components may be included to maintain the surface of target 24 at a desired distance from primary laser 10 so as both to maintain the focal point for primary laser emission 12 as well as the spatial relationship of electromagnetic fields 74, 76, 78, 80, and 82 with the target surface so as to retain consistent effects of these fields on the particles within the ejecta plume. In the embodiment shown in FIG. 1, this can be accomplished through a screw mechanism 118, which moves a pinion bar or rod 120, which can move target 24 forward as the target surface is ablated by laser 12. One of skill in the art will recognize that other mechanisms can be used as well. This same mechanism can be used to selectively increase or decrease the distance between the one or more electromagnetic fields and the target surface (e.g., between distances $D_1$ and $D_3$ as illustrated in FIG. 3) in order to selectively produce metal nanoparticles that are more coral-shaped or more spherical-shaped, as described herein.

A detector 122 can be used to monitor the position of the face or surface of target 24 by multiple known methods, including by monitoring the first electromagnetic field 74 for a slight interruption by the target face. Conversely, rather than moving target 24, the focal point for laser 12 and the position of electromagnetic fields 74, 76, 78, 80, and 82 can be changed as the target face moves due to the loss of material from repeated ablations. Similarly, rather than using large targets, small and thin targets can be utilized, or the same effect can be achieved if the targets are routinely changed. In yet a further embodiment, multiple targets can be loaded into a target containment vessel 124, which can act in conjunction with screw mechanism 118 and pinion bar 120 to allow for multiple targets to be ablated (and moved, positioned, and/or oriented as needed) without the need to manually insert a new target 24 into chamber 20.

As nanoparticles exit the gradient electric field(s), the process can produce nanoparticles with high $\xi$-potential (preferably at least 30 mV for spherical particles). This means that these nanoparticles, when suspended within any liquid, including any polar liquid such as water, exert uniform forces on each other and thereby remain suspended in solution without the need for any added surfactants (e.g., at concentrations of up to about 1 ppm, 10 ppm, 25 ppm, 50 ppm, 75 ppm, 100 ppm, 150 ppm, 200 ppm, or 250 ppm metal nanoparticles). The lack of surfactants allows introduction of these nanoparticles into applications where the presence of the surfactants would otherwise prove problematic, such as biological systems.

When utilizing a liquid as the carrier for the nanoparticles, any organic, non-polar compound can be used, as well as polar solutions including alcohols and water. Preferably, the selected liquid is free from ions and particulate matter to prevent unwanted agglomeration of nanoparticles to impurities within the liquid. When using water, multiple methods exist to remove ionic and particulate matter, including distillation and even multiple distillations, reverse osmosis, deionization techniques and ultrafiltration.

Figure 7:
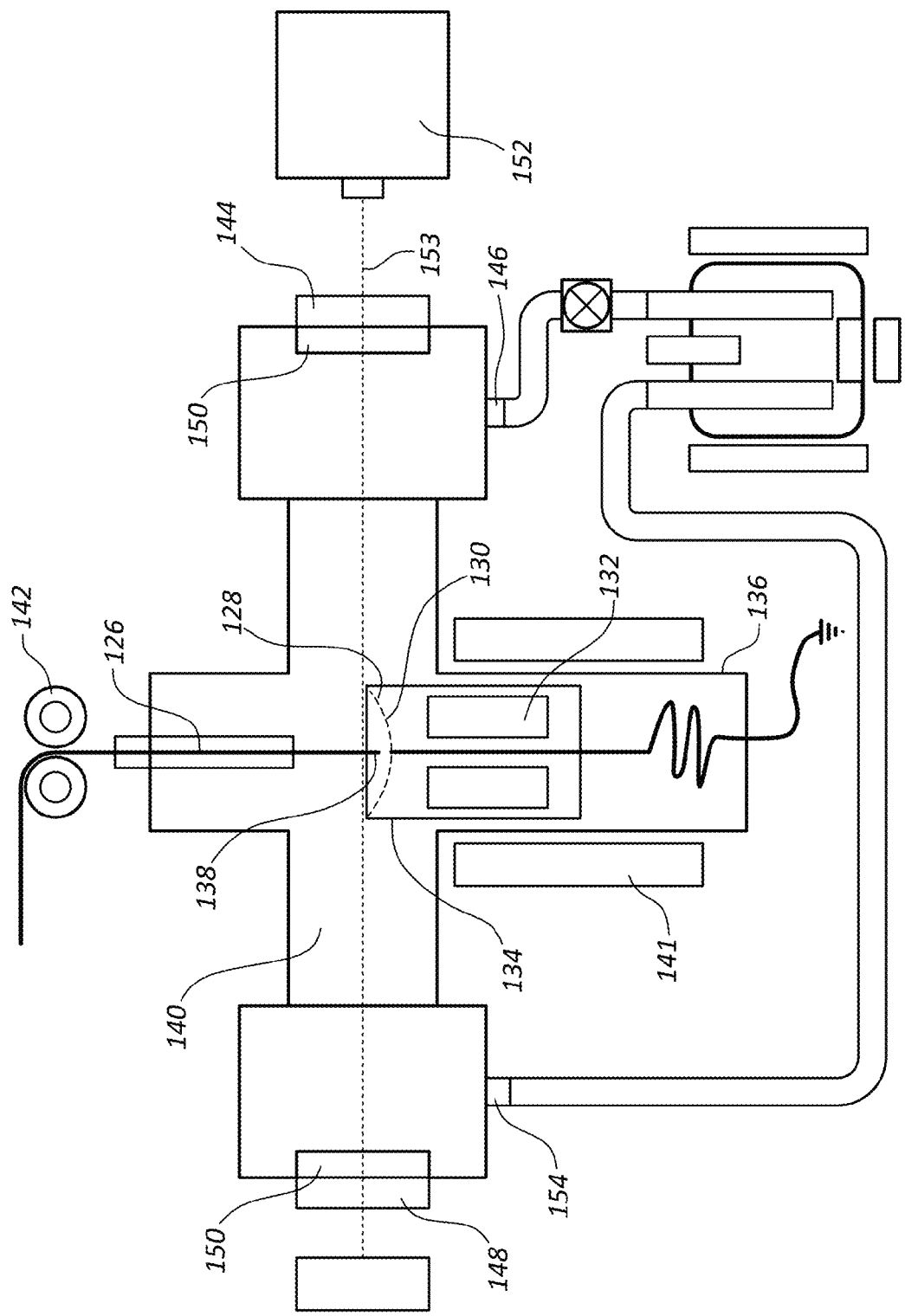
FIG. 7 schematically illustrates an apparatus for performing ablation using electrical discharge.
Figure 2:
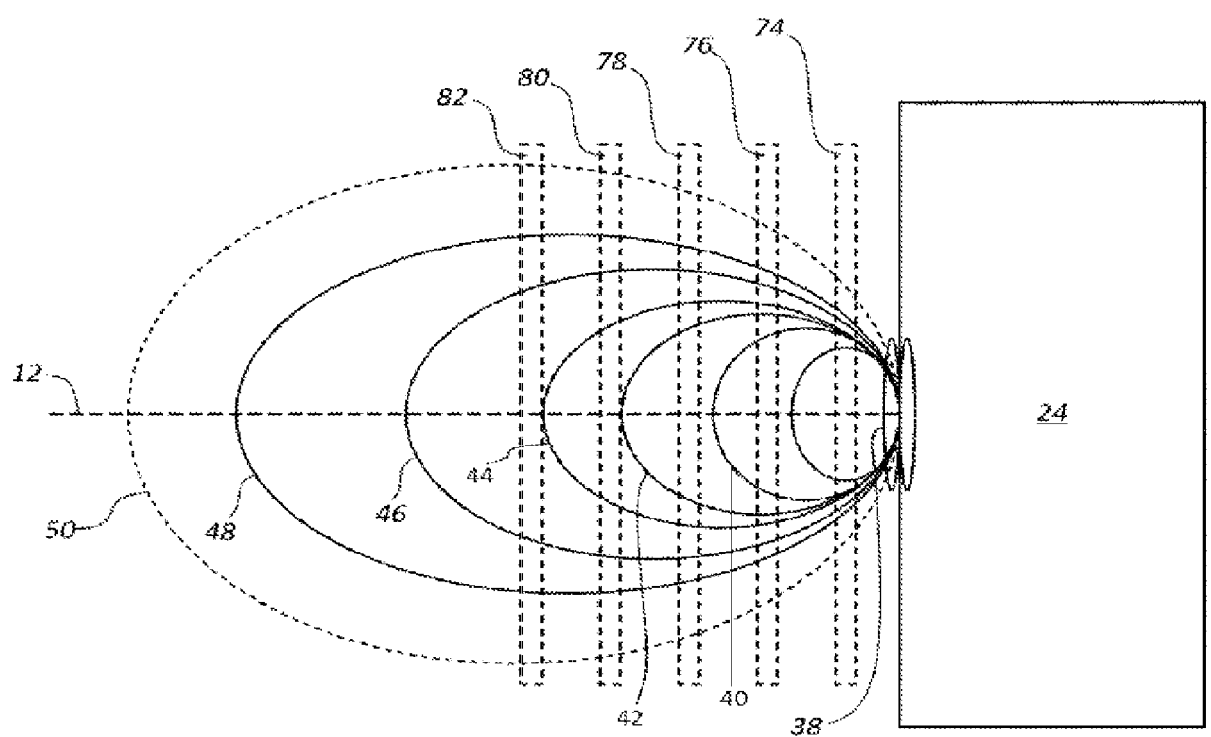

FIG. 7 schematically illustrates another embodiment of an apparatus for use in making nanoparticles, wherein the ejecta plume is created by an electric discharge process instead of laser ablation. Electric discharge processes can produce ablation in a vacuum system (where an ejecta plume is created). As will be readily understood by one skilled in the art, many of the same principles that apply to the laser ablation process can apply to a process to ablate material using electric discharge. For example, rather than a primary laser beam impacting a target, the electric discharge process utilizes a target anode 126 (e.g., wire) to create an ejecta plume near a surface 128 of a cathode material 130. In the embodiment illustrated in FIG. 7, this may be accomplished by placing cathode material 130 inside a holder 134 that contains a permanent magnet 132. Holder 134 can be held within a tube 136 that is part of a chamber 140. An electromagnet 141 extends around tube 136 and, when energized, creates a magnetic field that drives holder 134 upwards toward a tip 138 of target anode wire 126. The electric potential difference between anode wire 126 and cathode material 130 is sufficient to break down the resistance of the heavy atmosphere between surface 128 of cathode material 130 and tip 138 of anode wire 126, which discharge creates an ejecta plume of material from anode 126 that moves toward surface 128 of cathode material 130 and which then effectively bounces off of a curved cathode surface 128 and then moves through electromagnetic field(s) 153. The upward movement of holder 134 can be limited either by a piston-type control from the bottom of the holder or by physical interaction of cathode surface 128 with tip 138 of anode wire 126, or through other actuation means. As anode wire 126 loses mass through the ablation of tip 138, its length can be maintained by a wire feeding mechanism 142.

With the ejecta plume formed in the same location on each upward pulse of cathode material 130 and moving within the main cavity of chamber 140, an electromagnetic field 153, or preferably gradient electromagnetic fields 153, can then be introduced into the main cavity of chamber 140 through an optic window 144 at one end of chamber 140 while exiting through a second optic window 148 at the other end of chamber 140. As with the optics shown in FIG. 1, the input and output optics 144 and 148 can also include piezo-electrically controlled vibrators 150 to help prevent particle buildup on optics 144, 148. The frequency and strength of electromagnetic field or fields 153, whether created from a secondary laser 152 (or set of lasers) or other sources will be determined by the same parameters as those described above for the gradient electromagnetic fields in FIGS. 1 and 2.

Fluid flow can be introduced into chamber 140 through an input port 146 and exit through an output port 154, which fluid can be used to collect the nanoparticles after they have passed through the electromagnetic field(s) 153. Additionally, one of skill in the art can readily understand how this single arrangement of an anode wire and cathode material can be replicated, preferably in a linear manner, to utilize the same electromagnetic field or multiple gradient electromagnetic fields for multiple anode-cathode units in order to increase production of nanoparticles.

Consistent with the creation of an ejecta plume using laser ablation, the strength and duration of the electrical pulse from tip 138 of anode wire 126 will determine the total energy delivered (ET) per pulse and will be a function both of the target material's bonding energy (EB), the ionization energy (EI) as well as the number of total atoms/molecules to be contained within the desired shape of the final nanoparticle, which spherical- or coral-shaped. As with the apparatus shown in FIG. 1, coral-shaped metal nanoparticles can be formed instead of spherical-shaped metal nanoparticles by increasing the distance between electromagnetic field(s) 153 and tip 138 of anode material 126.

Even with the attempt to control particle size through precise energy delivery to the target surface, as with the ejecta plume created by laser ablation, the plume will contain a distribution of uncharged, nonionic particles ranging in size from small clusters of single digit atoms/molecules to nanoparticles of generally desired size as well as many larger particles. Further, because the electrical discharge method will almost always utilize metallic targets (because they act as the anode of the electric circuit), even though the energy delivered to the target will be less than the target's ionization energy, the initial ejecta plume may likely also contain some ionized, individual atoms. However, because anode target wire 126 is an anode, the ionized atoms will readily be pulled back to anode target 126 and reabsorbed into the crystalline matrix of the material.

Similarly, control of the velocity of the ejecta plume can also be accomplished through use of the fluid pressure within the reaction chamber in the same manner as discussed above with the laser ablation method.

Exemplary Uses

The nanoparticle compositions can be used for any desired purpose. Examples of antimicrobial compositions and methods of making and using antimicrobial compositions are disclosed in U.S. Provisional Application No. 62/054,152, filed Sep. 23, 2014, in the name of William Niedermeyer, and entitled "ANTIMICROBIAL COMPOSITIONS AND METHODS," which is incorporated by reference. In some embodiments, antimicrobial compositions may comprise a carrier and a plurality of metal nanoparticles having a particle size and a particle size distribution selected so as to selectively and preferentially kill one of a virus, a bacterium, or a fungus. In some embodiments, anti-viral compositions comprise metal nanoparticles having a particle size of about 8 nm or less, or about 1 nm to about 7 nm, or about 2 nm to about 6.5 nm, or about 3 nm to about 6 nm. In some embodiments, anti-bacterial compositions can include metal nanoparticles having a particle size of about 3 nm to about 14 nm, or about 5 nm to about 13 nm, or about 7 nm to about 12 nm, or about 8 nm to about 10 nm. In some embodiments, anti-fungal compositions can include metal nanoparticles having a particle size of about 9 nm to about 20 nm, or about 10 nm to about 18 nm, or about 11 nm to about 16 nm, or about 12 nm to about 15 nm. Within any of the foregoing size ranges, it is possible to select "designer antimicrobial particles" of specific size that are particularly effective in targeting a specific microbe.

Examples of fabrics and other fibrous materials that have been treated with nanoparticles, including spherical-shaped and coral-shaped nanoparticles, are disclosed in U.S. Provisional Application No. 62/054,182, filed Sep. 23, 2014, in the name of William Niedermeyer, and entitled "NANOPARTICLE TREATED FABRICS, FIBERS, FILAMENTS, AND YARNS AND RELATED METHOD," which is incorporated by reference. The nanoparticle treated fibrous articles can exhibit good antimicrobial activity while remaining stable over time (i.e., in which the nanoparticles can remain adhered to the fibrous substrate surface without covalent bonds, ionic bonds, or physical encapsulation.

Examples of how nanoparticle compositions can be used to treat plant diseases, such as citrus greening, are disclosed in U.S. Provisional Application No. 62/054,215, filed Sep. 23, 2014, in the name of William Niedermeyer, and entitled "COMPOSITIONS AND METHODS FOR TREATING PLANT DISEASES," which is incorporated by reference. An infected plant part can be temporarily removed from the plant, treated with a nanoparticle composition, and then grafted back onto the plant.

Examples of how nanoparticle compositions can be used as fuel additives are disclosed in U.S. Provisional Application No. 62/054,201, filed Sep. 23, 2014, in the name of William Niedermeyer, and entitled "FUEL ADDITIVE COMPOSITION AND RELATED METHODS," which is incorporated by reference.

Examples of how nanoparticle compositions can be used to treat or prevent Ebola virus disease are disclosed in U.S. Provisional Application No. 62/054,154, filed Sep. 23, 2014, in the name of William Niedermeyer, and entitle "ANTIVIRAL COMPOSITIONS AND METHODS FOR TREATMENT OF EBOLA VIRUS DISEASE," which is incorporated by reference.

Carriers

In some embodiments, a nanoparticle composition includes a carrier for delivering the metal nanoparticles onto or into a living or non-living substrate. The carrier can be a liquid, gel, or solid. Some carriers may be more suitable than others depending on the living or non-living substrate being treated. For example, the solubility characteristics of the carrier can be selected to maximize or otherwise provide a desired diffusion throughout a substrate and/or other organism or object coming into contact with the substrate.

Examples of compounds that can be used as carriers include, but are not limited to, water, alcohols, ketones, esters, citrus oils, essential oils, vegetable and other plant and natural oils, triglycerides, ethers, organic solvents, methanol, ethanol, isopropyl alcohol, other alcohols, glycols, glycerin, polyols, 1,3-propandiol, petroleum jelly, waxes, polymers, polymerizable materials, and surfactants.

In one embodiment, the carrier is a cream or lotion including a glycerin and/or stearic acid cream base optionally containing oils such as coconut oil, olive oil, grape seed oil, shea butter, mango butter, and/or vitamin E oil along with an emulsifying wax.

In other embodiments the carrier is a water or combined water and alcohol solution which itself contains a micro to millimolar concentration of a separate stabilizing agent dissolved into the carrier so as to maintain the nanoparticles within the overall composition.

Exemplary carriers for nasal or pulmonary aerosol or inhalation administration include solutions in saline which can contain, for example, benzyl alcohol or other suitable preservatives, absorption promoters to enhance bioavailability, and/or other solubilizing or wetting or dispersing agents, such as glycerin, a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g. dextran sulfate); and glycoaminoglycans and glycosaminoglycan-like compounds (e.g., hyaluronic acid), for example. In some embodiments, the nanoparticles, additional stabilizing agents and/or carriers are formulated as dry powders (e.g., powders useful for administering with dry powder inhalers).

Exemplary aerosols useful for nasal and/or inhalation administration include a vaporizable propellant, such as low molecular weight hydrofluorocarbons or hydrocarbons that are liquid when constrained in a suitable container and are biocompatible and non-irritating. Ingredients such as water, alcohol, propylene glycol, and polyethylene glycols can be additionally included. Other embodiments, also useful for nasal and/or inhalation administration, are provided as sprays (e.g., omitting an aerosol propellant). Such spray formulation may be provided as a solution, suspension, or emulsion capable of forming a fine mist for administration, and in some embodiments, may include saline and/or be isotonic.

Exemplary injectable solutions include an aqueous emulsion or oleaginous suspension or saline solution (e.g., isotonic, hypotonic, or hypertonic, optionally including dextrose and/or other electrolytes or additives). Such compositions can also include suitable dispersing or wetting agents. The sterile injectable preparation may also be formed in a non-toxic parenterally acceptable diluent or solvent, such as a solution in 1,2-propanediol (propylene glycol). Additional examples include solutions or suspensions which can contain, for example, suitable non-toxic diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Gels known in the art can be used as carriers, such as gels containing one or more of the foregoing liquid components together with known gelling agents. Gel compositions can more easily adhere to a living or non-living substrate being treated. An exemplary gel carrier can include mineral oil gelled with polyethylene.

Solid carriers can be used for different reasons, such as to elute nanoparticles into or onto a substrate over time. Examples of solid carriers include, but are not limited to, polymers, rubbers, elastomers, foams, and gums. Depending on the characteristics of the substrate to be treated and the desired rate of elution, one of skill in the art can select an appropriate solid carrier material.

In some embodiment, a nanoparticle composition can be formulated so that the metal nanoparticles are included in a concentration so that a measured quantity of the nanoparticle composition, when applied onto or into substrate, will provide a predetermined concentration or quantity of metal nanoparticles. The nanoparticle composition can have a higher concentration of nanoparticles that become diluted when mixed with other liquids applied to or naturally contained within the substrate. Depending on the substrate being treated, the nature of the nanoparticles being added, and the type of carrier being used, a nanoparticle composition may contain about 10 ppb, 15 ppb, or 0.5 ppm to about 100 ppm of metal nanoparticles by weight, or about 1 ppm to about 50 ppm, or about 2 ppm to about 25 ppm, or about 3 ppm to about 20 ppm metal nanoparticles by weight.

In some embodiments, nanoparticle compositions can also include one or more optional components or adjuvents to provide desired properties, including, but not limited to food, vitamins, minerals, antimicrobial agents, electrolytes, moisturizers, emollients, antiseptics, and/or plant extracts.

In some embodiments, the carrier may also function as, or may include, a stabilizing agent. For example, in some embodiments it may be desirable to have different specifically sized nanoparticles within the same solution to take advantage of each of the different properties and effects of the different particles. However, when differently sized particles are mixed into a single solution, the overall long-term stability of these particles within that single solution may be substantially diminished as a result of unequal forces exerted on the various particles causing eventual agglomeration of the particles. This phenomenon may become even more pronounced when that solution is either heated or cooled significantly above or below standard room temperature conditions.

Examples of stabilizing agents include alcohols (e.g., ethanol, propanol, butanol, etc.), polyphenols (e.g., arjuna bark extract, grape seed extract, etc.), mono-glycerides, di-glycerides, or triglycerides (e.g., grape seed oil, coconut oil, and the like), oils (e.g., lavender), other terpenes, amine compounds (e.g., mono-, di-, or tri-ethanol amine), carbohydrates (e.g., sucrose, fructose), liposomes, creams, other emulsions, and other polymers.

In some embodiments, stabilizing agents are dissolved within a separate carrier in the micro- to milli-molar concentration range with the upper range limitation typically being constrained not by efficacy but by product cost.

These various stabilizing agents have the capacity to hold the at least two differently sized and/or shaped nanoparticles in suspension and deliver these nanoparticles into or onto a substrate without so powerfully retaining the nanoparticles so as to diminish the effectiveness of the nanoparticles.

Antimicrobial Activity

By way of example, one way that nanoparticles can kill or denature a microbe is by catalyzing the cleavage of disulfide (S—S) bonds within a vital protein or enzyme. In the case of bacteria or fungi, the cleavage of disulfide bonds and/or cleavage of other chemical bonds of vital proteins or enzymes may occur within the cell interior and thereby killing the microbe in this manner. Such catalytic cleavage of disulfide (S—S) bonds is facilitated by the generally simple protein structures of microbes, in which many vital disulfide bonds are on exposed and readily cleaved by catalysis. Another mechanism by which metal (e.g., silver) nanoparticles can kill microbes is through the production of active oxygen species, such as peroxides, which can oxidatively cleave protein bonds, including but not limited to amide bonds. In the case of viruses, spherical-shaped and coral-shaped metal nanoparticles can alternatively deactivate viruses by attaching to glycoproteins and/or catalyzing protein denaturing reactions in the protein coat so that the virus is no longer able to attach to a host cell and/or inject genetic material into the host cell. Because very small nanoparticles can pass through a virus, denaturing of the protein coat may occur within the interior of the virus. A virus that is rendered unable to attach to a host cell and/or inject genetic material into the host cell is essentially inactive and no longer pathogenic.

Notwithstanding the lethal nature of nonionic metal nanoparticles relative to microbes, they can be relatively harmless to humans, mammals, and healthy mammalian cells, which contain much more complex protein structures compared to simple microbes in which most or all vital disulfide bonds are shielded by other, more stable regions of the protein. In many cases nonionic nanoparticles do not interact with or attach to human or mammalian cells, remain in and follow fluid flow, do not cross bathers, remain in the vascular system, and can be quickly and safely expelled through the urine without damaging kidneys or other cells.

In the particular case of silver (Ag) nanoparticles, the interaction of the silver (Ag) nanoparticle(s) within a microbe has been demonstrated to be particularly lethal without the need to rely on the production of silver ions ($Ag^+$) to provide the desired antimicrobial effects, as is typically the case with conventional colloidal silver compositions. The ability of silver (Ag) nanoparticles to provide effective microbial control without any significant release of toxic silver ions (Ag$^+$) into the surrounding environment is a substantial advancement in the art.

EXAMPLES

The following examples and comparative are given to illustrate various embodiments within, and aspects of, the scope of the present invention. These are given by way of example only, and it is understood that the following examples are not comprehensive or exhaustive of the many types of embodiments of the present invention that can be prepared in accordance with the present invention.

Example 1

Spherical Nanoparticles

A silver (Ag) target was held within a chamber through which flowed triple distilled deionized water. The silver (Ag) target was ablated using a primary laser with a 1064 nm wavelength at 80 mJ with a 1 mm focal spot size and with 9 nanosecond pulse lengths. The secondary laser was a continuous 532 nm laser with 0.5 W power going into a diffraction grating, which created three distinct electromagnetic fields in front of the silver (Ag) target. The process created 10 nm mean diameter silver (Ag) nanospheres, with 99+% of those nanospheres being within ±1 nm of the mean diameter.

Example 2

Spherical Nanoparticles

A silver (Ag) target was held within a chamber through which flowed triple distilled deionized water. The silver (Ag) target was ablated using a primary laser with a 1064 nm wavelength at 620 mJ with a 6 mm focal spot size and with 3.7 nanosecond pulse lengths. The secondary laser was a continuous 532 nm laser with 0.5 W power going into a diffraction grating, which created five distinct electromagnetic fields in front of the silver (Ag) target. The process created 14 nm mean diameter silver (Ag) nanospheres, with 99+% of those nanospheres being within ±1 nm of the mean diameter.

Example 3

Spherical Nanoparticles

A silver (Ag) anode wire target was ablated through a high voltage (800 V) between the target anode and a grounded silver (Ag) cathode. Both were submerged in a chamber through which flowed triple distilled deionized water. The secondary laser was a continuous 1064 nm laser with 5 W power that was not divided with any diffraction grating optics. The process created 10 nm mean diameter Ag nanospheres, with 99+% of those nanospheres being within ±1 nm of the mean diameter.

Example 4

Spherical Nanoparticles

A copper (Cu) target was held within a chamber through which flowed triple distilled deionized water. The copper (Cu) target was ablated using a primary laser with a 1064 nm wavelength at 80 mJ with a 1 mm focal spot size and with 9 nanosecond pulse lengths. The secondary laser was a continuous 264 nm laser with 0.25 W power going into a diffraction grating which created three distinct electromagnetic fields in front of the copper (Cu) target. The process created 8 nm mean diameter copper (Cu) nanospheres, with 99+% of those nanospheres being within ±1 nm of the mean diameter.

Example 5

Coral Nanoparticles

According to some embodiments, laser ablation of a metal target surface (e.g., silver) can be performed by a Nd-YAG laser at 1064 nm wavelength using 3.9 nanosecond pluses to deliver approximately 500 mJ energy per pulse. The secondary laser was a continuous 532 nm laser with 0.5 W power going into a diffraction grating, which created three distinct electromagnetic fields in front of the gold (Au) target. The distance of the secondary laser in front of the surface of the gold (Au) target was increased from 1 mm (Example 1) to 3 mm, which created coral-shaped nanoparticles instead of spherical-shaped nanoparticles as in Example 1. The process created gold (Au) nanoparticles having a mean diameter between 25-30 nm, which nanocoral, with 99+% of those nanoparticals being within 10% of the mean diameter.

Example 6

Coral Nanoparticles

A gold (Au) target was held within a chamber through which flowed triple distilled deionized water. The gold (Au) target was ablated using a primary laser with a 1064 nm wavelength at 80 mJ with a 3 mm focal spot size and with 9 nanosecond pulse lengths. The secondary laser was a continuous 532 nm laser with 0.5 W power going into a diffraction grating, which created three distinct electromagnetic fields in front of the gold (Au) target. The distance of the secondary laser in front of the surface of the gold (Au) target was increased from 1 mm (Example 1) to 3 mm, which created coral-shaped nanoparticles instead of spherical-shaped nanoparticles as in Example 1. The process created coral-shaped gold (Au) nanoparticles having a mean diameter between 70-80 nm, with 99+% of those nanoparticals being within 10% of the mean diameter.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:
1. A nanoparticle composition comprising:
    a plurality of spherical-shaped nanoparticles; and
    a plurality of coral-shaped metal nanoparticles, each coral-shaped metal nanoparticle having a non-uniform cross section and a globular structure formed by multiple, non-linear strands joined together without right angles.

2. A nanoparticle composition as in claim 1, wherein the nanoparticle composition has a mass ratio of spherical-shaped nanoparticles to coral-shaped nanoparticles of about 5:1 to about 20:1.

3. A nanoparticle composition as in claim 1, wherein the nanoparticle composition has a particle number ratio of spherical-shaped nanoparticles to coral-shaped nanoparticles of about 50:1 to about 200:1.

4. A nanoparticle composition as in claim 1, wherein the spherical-shaped nanoparticles have a diameter of about 40 nm or less.

5. A nanoparticle composition as in claim 1, wherein the spherical-shaped nanoparticles have a mean diameter and wherein at least 99% of the spherical-shaped nanoparticles have a diameter within about 30% of the mean diameter.

6. A nanoparticle composition as in claim 1, wherein the spherical-shaped nanoparticles have a mean diameter and wherein at least 99% of the spherical-shaped nanoparticles have a diameter within ±3 nm of the mean diameter.

7. A nanoparticle composition as in claim 1, wherein the spherical-shaped nanoparticles have a ξ-potential of at least about 10 mV.

8. A nanoparticle composition as in claim 1, wherein the coral-shaped metal nanoparticles have a length in a range of about 15 nm to about 100 nm.

9. A nanoparticle composition as in claim 1, wherein the coral-shaped metal nanoparticles have a mean length and wherein at least 99% of the coral-shaped metal nanoparticles have a length within about 30% of the mean length.

10. A nanoparticle composition as in claim 1, wherein the coral-shaped nanoparticles have a ξ-potential of at least about 10 mV.

11. A nanoparticle composition as in claim 1, wherein the nanoparticle composition has a concentration of spherical-shaped nanoparticles in a range of about 10 ppb to about 500 ppm and a concentration of coral-shaped nanoparticles in a range of about 10 ppb to about 500 ppm.

12. A nanoparticle composition as in claim 1, wherein the spherical-shaped nanoparticles and the coral-shaped nanoparticles independently comprise at least one metal selected from the group consisting of gold, platinum, silver, palladium, rhodium, osmium, ruthenium, rhodium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, and alloys thereof.

13. A nanoparticle composition as in claim 1, wherein the spherical-shaped nanoparticles comprise silver and the coral-shaped nanoparticles comprise gold.

14. A method of using a nanoparticle composition, comprising applying a nanoparticle composition to a substrate, the nanoparticle composition including:
  a plurality of spherical-shaped nanoparticles; and
  a plurality of coral-shaped metal nanoparticles, each coral-shaped metal nanoparticle having a non-uniform cross section and a globular structure formed by multiple, non-linear strands joined together without right angles.

15. A method as in claim 14, wherein the substrate is a non-living object.

16. A method as in claim 14, wherein the substrate is a living organism.

17. A method as in claim 14, wherein the nanoparticle composition is a multi-part composition and wherein the spherical-shaped nanoparticles and the coral-shaped nanoparticles are applied sequentially.

18. A method of manufacturing a nanoparticle composition, comprising:
  obtaining spherical-shaped nanoparticles;
  obtaining coral-shaped nanoparticles, each coral-shaped metal nanoparticle having a non-uniform cross section and a globular structure formed by multiple, non-linear strands joined together without right angles; and
  combining the spherical-shaped nanoparticles with the coral-shaped nanoparticles to form the nanoparticle composition.

19. A method as in claim 18, further comprising ablating a target in a heavy atmosphere to form an ejecta plume, and applying an electromagnetic field to the ejecta plume in order to cause the ejecta plume to form the spherical-shaped nanoparticles and the coral-shaped nanoparticles.

20. A method as in claim 19, further comprising:
  selectively forming the spherical-shaped nanoparticles by positing the electromagnetic field at a first distance in front of the target in order to promote formation of spherical-shaped nanoparticles; and
  selectively forming the coral-shaped nanoparticles by positing the electromagnetic field at a second distance in front of the target in order to promote formation of coral-shaped nanoparticles.

* * * * *

UNITED STATES PATENT AND TRADEMARK OFFICE
CERTIFICATE OF CORRECTION

PATENT NO. : 9,434,006 B2
APPLICATION NO. : 14/861318
DATED : September 6, 2016
INVENTOR(S) : Niedermeyer It is certified that error appears in the above-identified patent and that said Letters Patent is hereby corrected as shown below:

On the Title Page

Item (56), References Cited, U.S. Patent Documents, Page 2, change "Halas et al." to --Marsh--

Item (56), References Cited, Other Publications, Page 2, change "14/298,593" to --14/298,594--

In the Drawings

Sheet 2, replace Fig. 2 with the figure depicted herein below, wherein the reference 42 has been changed to 44 as shown on the attached page Sheet 2, replace Fig. 2 with the figure depicted herein below, wherein the reference 40 has been changed to 42 as shown on the attached page Sheet 2, replace Fig. 2 with the figure depicted herein below, wherein the reference number 40 has been added as shown on the attached page In the Specification Column 5
Line 6, change "fields at a distance in from of the metal target" to --fields at a distance from the metal target--

Signed and Sealed this
Fourteenth Day of February, 2017

Michelle K. Lee
*Director of the United States Patent and Trademark Office*